US012673924B2

(12) United States Patent
Treston et al.

(10) Patent No.: US 12,673,924 B2
(45) Date of Patent: Jul. 7, 2026

(54) VALIOLAMINE DERIVATIVES AS GLUCOSIDASE INHIBITORS

(71) Applicant: Emergent Product Development Gaithersburg Inc., Gaithersburg, MD (US)

(72) Inventors: Anthony M. Treston, Gaithersburg, MD (US); Kelly Lyn Warfield, Gaithersburg, MD (US)

(73) Assignee: EMERGENT PRODUCT DEVELOPMENT GAITHERSBURG INC., Gaithersburg, MD (US)

( * ) Notice: Subject to any disclaimer, the term of this patent is extended or adjusted under 35 U.S.C. 154(b) by 386 days.

(21) Appl. No.: 18/279,920

(22) PCT Filed: Mar. 2, 2022

(86) PCT No.: PCT/US2022/018519
§ 371 (c)(1),
(2) Date: Sep. 1, 2023

(87) PCT Pub. No.: WO2022/187361
PCT Pub. Date: Sep. 9, 2022

(65) Prior Publication Data
US 2024/0174619 A1 May 30, 2024

Related U.S. Application Data

(60) Provisional application No. 63/201,194, filed on Apr. 16, 2021, provisional application No. 63/156,253, filed on Mar. 3, 2021.

(51) Int. Cl.

| | |
|---|---|
| ***C07H 15/22*** | (2006.01) |
| ***A61K 31/136*** | (2006.01) |
| ***A61K 31/27*** | (2006.01) |
| ***A61K 31/4192*** | (2006.01) |
| ***A61K 31/505*** | (2006.01) |
| ***A61K 31/7008*** | (2006.01) |
| ***C07C 215/44*** | (2006.01) |
| ***C07C 217/08*** | (2006.01) |
| ***C07C 229/10*** | (2006.01) |
| ***C07C 247/16*** | (2006.01) |
| ***C07C 271/20*** | (2006.01) |
| ***C07D 239/26*** | (2006.01) |
| ***C07D 249/06*** | (2006.01) |
| ***C07D 257/04*** | (2006.01) |

(52) U.S. Cl.
CPC .......... *C07D 239/26* (2013.01); *A61K 31/136* (2013.01); *A61K 31/27* (2013.01); *A61K 31/4192* (2013.01); *A61K 31/505* (2013.01); *C07C 215/44* (2013.01); *C07C 217/08* (2013.01); *C07C 229/10* (2013.01); *C07C 247/16* (2013.01); *C07C 271/20* (2013.01); *C07D 249/06* (2013.01); *C07D 257/04* (2013.01)

(58) Field of Classification Search
CPC ....... C07H 15/22; A61K 31/7008; A61P 3/10; A61P 31/12
USPC .......................................... 536/1.11; 514/23
See application file for complete search history.

(56) References Cited

U.S. PATENT DOCUMENTS

| | | | | |
|---|---|---|---|---|
| 4,824,943 | A * | 4/1989 | Horii | C07C 49/753 536/124 |
| 4,923,975 | A | 5/1990 | Kameda et al. | |
| 2012/0014923 | A1 | 1/2012 | Isa et al. | |
| 2018/0344784 | A1 | 12/2018 | Huang et al. | |
| 2019/0321326 | A1 | 10/2019 | Hsu et al. | |

FOREIGN PATENT DOCUMENTS

| | | | |
|---|---|---|---|
| CN | 108003042 | A | 5/2018 |
| CN | 108059603 | A | 5/2018 |
| EP | 0056194 | A1 | 7/1982 |
| EP | 0240175 | A1 | 10/1987 |
| WO | WO-9517903 | A1 | 7/1995 |
| WO | WO-9640700 | A1 | 12/1996 |

OTHER PUBLICATIONS

Ogawa, S., et al., "Development and Medical Application of Unsaturated Carbaglycosylamine Glycosidase Inhibitors", Mini reviews in medicinal chemistry, 679-691, Bentham Science Publishers, Netherlands (Jul. 2007).

Kuriyama, C., et al., "In vitro inhibition of glycogen-degrading enzymes and glycosidases by six-membered sugar mimics and their evaluation in cell cultures", Bioorganic & Medicinal Chemistry, 16(15):7330-7336, Elsevier, Netherlands (Aug. 2008).

International Search Report and Written Opinion for International Application No. PCT/US2022/018519, Commissioner for Patents, United States, mailed on Jul. 26, 2022, 10 pages.

Horii, S., et al., "Synthesis and α-D-Glucosidase Inhibitory Activity of N-Substituted Valiolamine Derivatives as Potential Oral Antidiabetic Agents," J. Med. Chem. 29:1038-1046, American Chemical Society, United States (1986).

Karade, S.S., et al., "N-Substituted Valiolamine Derivatives as Potent Inhibitors of Endoplasmic Reticulum α-Glucosidases I and II with Antiviral Activity," J. Med. Chem. 64:18010-18024, American Chemical Society, United States (2021).

* cited by examiner

*Primary Examiner* — Charanjit Aulakh
(74) *Attorney, Agent, or Firm* — Sterne, Kessler, Goldstein & Fox P.L.L.C.

(57) ABSTRACT

This disclosure is directed to N-substituted valiolamine compounds, their use as glycosidase inhibitors, and in methods of treating diseases or conditions in which glycosidase inhibition provides benefit.

19 Claims, No Drawings

Specification includes a Sequence Listing.

VALIOLAMINE DERIVATIVES AS GLUCOSIDASE INHIBITORS

REFERENCE TO A SEQUENCE LISTING

The instant application contains a Sequence Listing which has been submitted in ASCII format via EFS-Web and is hereby incorporated by reference in its entirety. The Sequence Listing is being concurrently submitted via EFS-Web as an ASCII text file named 2479_2220001_Seqlisting_ST25.txt, was created on Apr. 5, 2021, and contains 20,775 bytes.

FIELD

Embodiments of the present disclosure generally relate to aminocyclitols—for example, N-substituted valiolamine compounds—and their use as glycosidase inhibitors. The present disclosure further provides methods of treating conditions and diseases, for which glycosidase inhibition provides benefit.

BACKGROUND

Valiolamine is an aminocyclitol (also called pseudoaminosugar) and is a natural product identified in the fermentation broth of *Streptomyces hygroscopicus* subsp *limoneus*. Certain valiolamine derivatives are capable of inhibiting α-glucosidase and are suitable as pharmaceutical agents for treating diabetes. Voglibose ((1S,2S,3R,4S,5S)-5-(1,3-dihydroxypropan-2-ylamino)-1-(hydroxymethyl)cyclohexane-1,2,3,4-tetraol), for example, is a derivative of valiolamine and is an alphα-glucosidase inhibitor used for lowering post-prandial blood glucose levels in people with diabetes mellitus. Voglibose delays the absorption of glucose thereby reducing the risk of macrovascular complications. Given the prevalence of diabetes and the need for treatment of other diseases and conditions that are responsive to inhibition of α-glucosidase, incuding, for example, certain viral diseases, there remains a need in the art for novel valiolamine derivatives.

BRIEF SUMMARY OF THE DISCLOSURE

The present disclosure is directed to N-substituted valiolamine compounds and their use as glycosidase inhibitors in treating diseases or conditions. More specifically, the present disclosure provides a compound according to Formula (I):

I

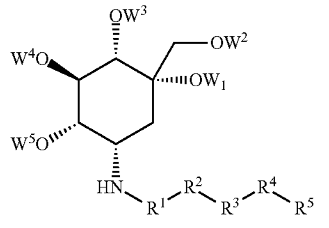

or a pharmaceutically acceptable salt thereof, wherein $W^1$-$W^5$ are each independently selected from the group consisting of —H, —C(═O)—$C_1$-$C_9$ alkyl, and —C(═O)O—$C_1$-$C_9$ alkyl;

$R^1$ is optionally substituted $C_1$-$C_9$ alkylene;

$R^2$ is absent or selected from the group consisting of —H, —NH—, —O—, —C(═O)—, and —NH—C(═O)O—;

$R^3$ is absent or selected from the group consisting of —O—, —C(═O)—, —C(═O)O—, and optionally substituted $C_1$-$C_6$ alkylene;

$R^4$ is absent or selected from the group consisting of —H, —NH—, and optionally substituted $C_1$-$C_6$ alkylene;

$R^5$ is absent, or is

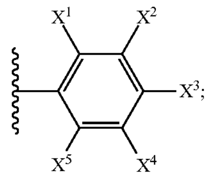

wherein $X^1$, $X^2$, $X^3$, $X^4$, and $X^5$ are each independently selected from the group consisting of —H, —$NO_2$, —$N_3$, optionally substituted $C_2$-$C_{12}$ heterocycle, and optionally substituted $C_1$-$C_{12}$ heteroaryl.

In some embodiments, $W^1$-$W^5$ are each independently —H.

In some embodiments, $R^1$ is a $C_1$-$C_9$ alkylene.

In some embodiments, the $C_1$-$C_9$ alkylene is selected from the group consisting of —$CH_2$—, —$CH_2$—$CH_2$—, —$(CH_2)_3$—, —$(CH_2)_4$—, —$(CH_2)_5$—, —$(CH_2)_6$—, —$(CH_2)_7$—, —$(CH_2)_8$—, and —$(CH_2)_9$—.

In some embodiments, the $C_1$-$C_9$ alkylene is —$(CH_2)_2$—.

In some embodiments, the $C_1$-$C_9$ alkylene is —$(CH_2)_4$—.

In some embodiments, the $C_1$-$C_9$ alkylene is —$(CH_2)_5$—.

In some embodiments, the $C_1$-$C_9$ alkylene is —$(CH_2)_6$—.

In some embodiments, the $C_1$-$C_9$ alkylene is —$(CH_2)_9$—.

In some embodiments, $R^3$ is a $C_1$-$C_6$ alkylene.

In some embodiments, the $C_1$-$C_6$ alkylene is selected from the group consisting of —$CH_2$—, —$CH_2$—$CH_2$—, —$(CH_2)_3$—, —$(CH_2)_4$—, —$(CH_2)_5$—, and —$(CH_2)_6$—.

In some embodiments, the $C_1$-$C_6$ alkylene is —$CH_2$—.

In some embodiments, the $C_1$-$C_6$ alkylene is —$CH_2$—$CH_2$—.

In some embodiments, $R^4$ is a $C_1$-$C_6$ alkylene.

In some embodiments, the $C_1$-$C_6$ alkylene is selected from the group consisting of —$CH_2$—, —$CH_2$—$CH_2$—, —$(CH_2)_3$—, —$(CH_2)_4$—, —$(CH_2)_5$—, and —$(CH_2)_6$—.

In some embodiments, the $C_1$-$C_6$ alkylene is —$CH_2$—$CH_2$—.

In some embodiments, $R^5$ is

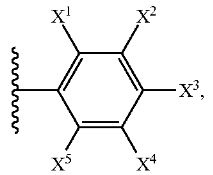

and $X^1$, $X^2$, $X^3$, $X^4$, and $X^5$ are each independently selected from the group consisting of —H, —$NO_2$, —$N_3$, an optionally substituted $C_2$-$C_{12}$ heterocycle, and a $C_1$-$C_{12}$ heteroaryl.

In some embodiments, the $C_1$-$C_{12}$ heteroaryl is selected from the group consisting of

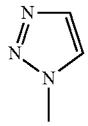, 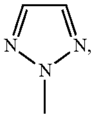, 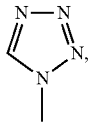 and 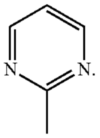

In some embodiments, $X^3$ is $—N_3$ or a $C_1$-$C_{12}$ heteroaryl.

In some embodiments, $X^3$ is $—N_3$.

In some embodiments, $X^3$ is a $C_1$-$C_{12}$ heteroaryl, and the $C_1$-$C_{12}$ heteroaryl is selected from the group consisting of

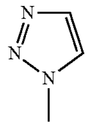, 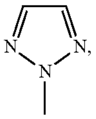, 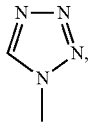 and 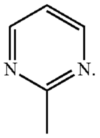

In some embodiments, $X^1$ is $—NO_2$.

In some embodiments, $X^2$, $X^4$, and $X^5$ are each —H.

In some embodiments, the compound is selected from the group consisting of:

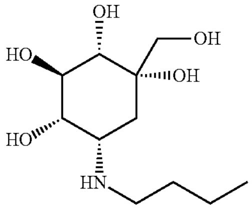,

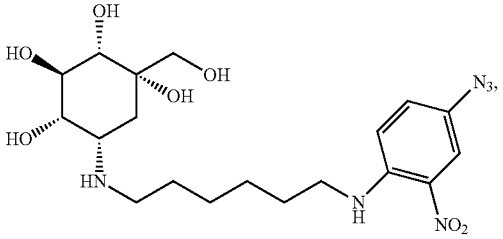

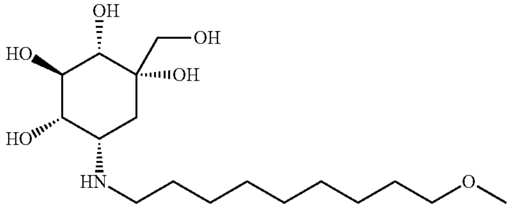,

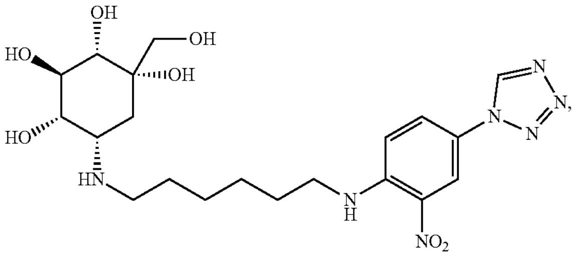

-continued

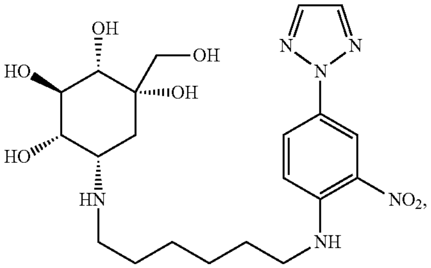

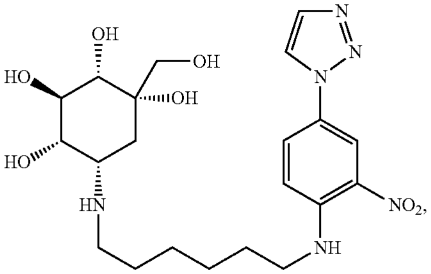

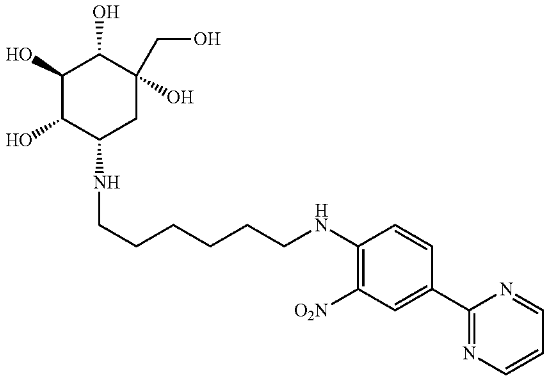,

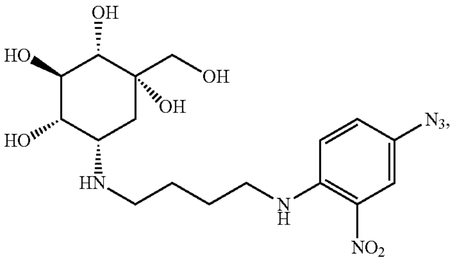

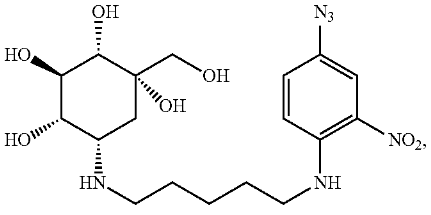

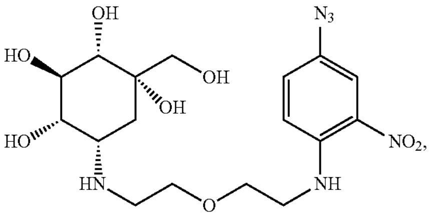

-continued

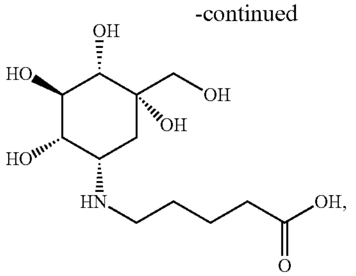

, and

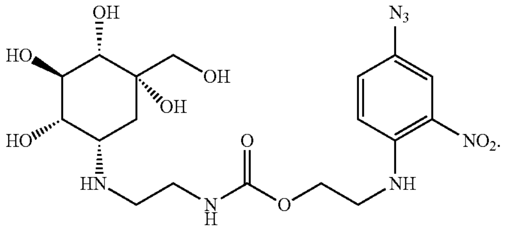

.

In some embodiments, a pharmaceutical composition comprises the compound and at least one pharmaceutically acceptable excipient.

In some embodiments, a method of treating diabetes comprises administering to a subject in need thereof, a therapeutically effective amount of the compound.

In some embodiments, the subject is a mammal.

In some embodiments, the subject is a human.

In some embodiments, the diabetes is Type 1 diabetes.

In some embodiments, the diabetes is Type 2 diabetes.

In some embodiments, a method for inhibiting glycosidase function comprises administering to a subject in need thereof a therapeutically effective amount of the compound.

In some embodiments, a method for treating or preventing a viral infection comprises administering to a subject in need thereof a therapeutically effective amount of the compound.

In some embodiments, the viral infection is selected from the group consisting of hepatitis C virus (HCV) infection, hepatitis B virus (HBV) infection, dengue virus (DENV) infection, Marburg virus (MARV) infection, Ebola virus (EBOV) infection, BVHV, human immunodeficiency virus (HIV) infection, influenza A infection, influenza B infection, encephalitis viruses infection, Zika virus infection, and yellow fever virus (YFV) infection.

In some embodiments, the encephalitis virus infection is eastern equine encephalitis viruses virus infection, western equine encephalitis virus infection, and Japanese encephalitis virus (JEV) infection.

In some embodiments, the viral infection is dengue virus infection

In some embodiments, the viral infection is an influenza virus infection

In some embodiments, the influenza virus infection is an influenza A virus infection.

In some embodiments, the influenza virus infection is an influenza B virus infection.

DETAILED DESCRIPTION

Definitions

The indefinite articles "a," "an," and "the" include plural references unless clearly contradicted or the context clearly dictates otherwise.

As used herein, the term "alkylene" as used by itself or as part of another group refers to a straight-chain or branched-chain aliphatic bivalent hydrocarbon containing one to nine carbon atoms, i.e., a $C_1$-$C_9$ alkylene, or the number of carbon atoms designated, e.g., a $C_1$ alkylene such as methylene ($—CH_2—$), a $C_2$ alkylene such as ethylene ($—CH_2—CH_2—$), a $C_3$ alkylene such as propylene ($—(CH_2)_3—$) etc. Non-limiting exemplary $C_1$-$C_9$ alkylene groups include $—CH_2—$, $—CH_2—CH_2—$, $—(CH_2)_3—$, $—(CH_2)_4—$, $—(CH_2)_5—$, $—(CH_2)_6—$, $—(CH_2)_7—$, $—(CH_2)_8—$, and $—(CH_2)_9—$. In some embodiments, the alkylene can be a $C_1$-$C_6$ alkylene. In other embodiments, the alkylene can be a $C_1$-$C_5$ alkylene. In another embodiment, the alkylene can be a $C_1$-$C_4$ alkylene. In still further embodiments, the alkylene can be a $C_1$-$C_3$ alkylene, i.e., methylene ($—CH_2—$), ethylene ($—CH_2—CH_2—$), or propylene ($—(CH_2)_3—$).

As used herein, the term "optionally substituted alkylene" by itself or as part of another group refers to an alkylene group that is either unsubstituted or substituted with one, two, or more substituents selected from the group consisting of $C_1$-$C_6$ alkyl, $C_1$-$C_6$ alkoxy, —OH, $—NH_2$, halogen, —SH, and $—NO_2—$.

The term "alkyl" as used herein by itself or as part of another group refers to a straight-chain or branched-chain aliphatic hydrocarbon containing one to twelve carbon atoms, i.e., a $C_1$-$C_{12}$ alkyl, or the number of carbon atoms designated, e.g., a $C_1$ alkyl such as methyl, a $C_2$ alkyl such as ethyl, etc. Non-limiting exemplary $C_1$-$C_6$ alkyl groups include methyl, ethyl, propyl, isopropyl, butyl, sec-butyl, tert-butyl, isobutyl, 3-pentyl, and hexyl. In some embodiments, the alkyl can be a $C_1$-$C_6$ alkyl. In other embodiments, the alkyl can be a $C_1$-$C_4$ alkyl. In another embodiment, the alkyl can be a $C_1$-$C_2$ alkyl. In still further embodiments, the alkyl can be a $C_1$-$C_3$ alkyl, i.e., methyl, ethyl, propyl, or isopropyl.

As used herein, the term "alkoxy" by itself or as part of another group refers to an alkyl group attached to a terminal oxygen atom. Non-limiting exemplary alkoxy groups include methoxy, ethoxy, tert-butoxy, and the like. In some embodiments, the alkyl is a $C_x$-$C_y$ alkyl, such as a $C_1$-$C_6$ alkyl and the resulting alkoxy is thus referred to as a "$C_1$-$C_6$ alkoxy." Non-limiting exemplary alkoxy groups include methoxy, ethoxy, and tert-butoxy. In some embodiments, the alkyl can be a $C_1$-$C_4$ alkyl group, providing a $C_1$-$C_4$ alkoxy.

As used herein, the term "halogen" by itself or as part of another group refers to —Cl, —F, —Br, or —I.

As used herein, the term "heterocycle" refers to saturated and partially unsaturated, e.g., containing one or two double bonds, cyclic groups containing one, two, or three rings having from three to fourteen ring members, i.e., a 3- to 14-membered heterocycle, wherein at least one carbon atom of one of the rings is replaced with a heteroatom. Each heteroatom in the heterocycle is independently selected from the group consisting of oxygen, sulfur, and nitrogen atoms, wherein the sulfur and nitrogen atoms can optionally be oxidized (i.e. to a sulfoxide, sulfone, or N-oxide, as appropriate), or optionally quaternized in the case of nitrogen. The term "heterocycle" further includes groups wherein a ring $—CH_2—$ is replaced with a —C(═O)—, such that the term "heterocycle" captures, for example, cyclic esters, cyclic ureido groups such as 2-imidazolidinone, and cyclic amide groups such as β-lactam, γ-lactam, δ-lactam, ε-lactam, and piperazin-2-one. In some embodiments, the heterocycle can be chosen from a 5- or 6-membered cyclic group containing one ring and one or two oxygen and/or nitrogen atoms. The heterocycle can be optionally linked to the rest of the molecule through any available carbon or nitrogen atom. Non-limiting exemplary heterocyclic groups include aziridinyl, azetidinyl, pyrrolidinyl, piperidinyl, piperazinyl, azepanyl, oxiranyl, oxetanyl, tetrahydrofuranyl, tetrahydrothienyl, tetrahydropyranyl, tetrahydrothiopyranyl, morpholinyl, thiomorpholinyl, thioxanyl, pyrrolinyl, 2H-pyranyl, 4H-pyranyl, dioxanyl, 1,3-dioxolanyl, pyrazolidinyl, pyrazolinyl, dihydropyranyl, dihydrothienyl, dihydrofuranyl, pyrazolidinyl, imidazolinyl, imidazolidinyl, dioxanyl, tetrahydropyranyl, 2-oxopyrrolidin-3-yl, piperazin-2-one, piperazine-2,6-dione, and 2-imidazolidinone.

As used herein, the term "heteroaryl" refers to an aromatic ring compound containing 5 or more ring members, of which, one or more is a heteroatom such as, but not limited to, N, O, and S. Non-limiting exemplary heteroaryl groups include pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, imidazolyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. In some embodiments, a heteroaryl group includes fused ring compounds and also includes heteroaryl groups that have other groups bonded to one of the ring members, such as alkyl groups, referred to as "substituted heteroaryl groups." The heteroatom(s) may also be in oxidized form, if chemically possible. The point of attachment of a given heteroaryl group can be any appropriate atom. Exemplary heteroaryl groups showing various points of attachment suitable for use in the present compounds are shown below:

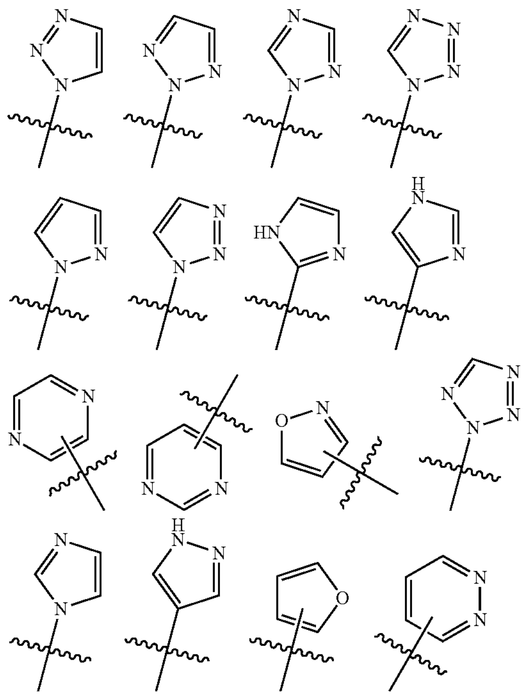

-continued

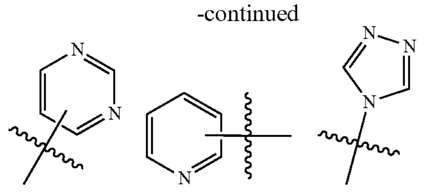

As used herein, the term "optional" or "optionally" means that the subsequently described circumstance may or may not occur, so that the description includes instances where the circumstance occurs and instances where it does not.

As used herein, the term "substituted" refers to independent replacement of one or more (typically 1, 2, 3, 4, or 5) hydrogen atoms on the substituted moiety with substituents independently selected from the group of substituents as specified for a particular group. In general, a non-hydrogen substituent can be any substituent that can be bound to an atom of the given moiety that is specified to be substituted.

As used herein, the phrase "pharmaceutically acceptable salt" refers to a salt formed with a compound described herein and a pharmaceutically acceptable acid. Pharmaceutically acceptable salts and methods for preparing salt forms are disclosed, for example, in Berge et al. (*J. Pharm. Sci.* 66:1-18, 1977). Examples of pharmaceutically acceptable acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts that can be formed with the compounds disclosed herein include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, glucoheptanoate, glycerolphsphate, hemisulfate, heptanoate, hexanoate, formate, succinate, fumarate, lactate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, thiocyanate, gluconate, methanesulfonate, ethanedisulfonate, benzene sulfonate, and p-toluenesulfonate salts.

Description

Described herein are compounds that include a compound according to Formula (I):

I

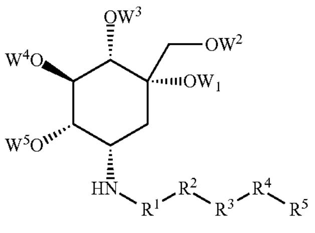

or a pharmaceutically acceptable salt thereof, wherein $W^1$-$W^5$ are each independently selected from the group consisting of —H, benzyl, —C(═O)—$C_1$-$C_9$ alkyl, and —C(═O)O—$C_1$-$C_9$ alkyl;

$R^1$ is optionally substituted $C_1$-$C_9$ alkylene;

$R^2$ is absent or selected from the group consisting of —H, —NH—, —O—, —C(═O)—, and —NH—C(═O)O—;

$R^3$ is absent or selected from the group consisting of —O—, —C(═O)—, —C(═O)O—, and optionally substituted $C_1$-$C_6$ alkylene;

$R^4$ is absent or selected from the group consisting of —H, —NH—, and optionally substituted $C_1$-$C_6$ alkylene; and $R^5$ is absent, or is

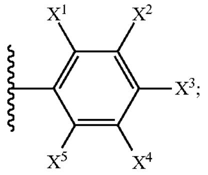

wherein $X^1$, $X^2$, $X^3$, $X^4$, and $X^5$ are each independently selected from the group consisting of —H, —$NO_2$, —$N_3$, optionally subsittued $C_2$-$C_{12}$ heterocycle, and optionally substituted $C_1$-$C_{12}$ heteroaryl.

In some embodiments, $W^1$-$W^5$ can each be independently selected from the group consisting of —H, —C(═O)—$C_1$-$C_9$ alkyl, and —C(═O)O—$C_1$-$C_9$ alkyl. In some embodiments, $W^1$-$W^5$ can each be independently —C(═O)—$C_1$-$C_9$ alkyl. In some embodiments, $W^1$-$W^5$ can each be independently —C(═O)O—$C_1$-$C_9$ alkyl. In some embodiments, $W^1$-$W^5$ can each be independently —H.

In some embodiments, le can be optionally substituted $C_1$-$C_9$ alkylene. In some embodiments, le can be selected from the group consisting of —$CH_2$—, —$CH_2$—$CH_2$—, —$(CH_2)_3$—, —$(CH_2)_4$—, —$(CH_2)_5$—, —$(CH_2)_6$—, —$(CH_2)_7$—, —$(CH_2)_8$—, and —$(CH_2)_9$—. In certain embodiments, $R^1$ can be —$CH_2$—. In certain embodiments, $R^1$ can be —$(CH_2)_2$—. In certain embodiments, $R^1$ can be —$(CH_2)_3$—. In certain embodiments, $R^1$ can be —$(CH_2)_4$—. In certain embodiments, $R^1$ can be —$(CH_2)_5$—. In certain embodiments, $R^1$ can be —$(CH_2)_6$—. In certain embodiments, $R^1$ can be —$(CH_2)_7$—. In certain embodiments, $R^1$ can be —$(CH_2)_8$—. In certain embodiments, $R^1$ can be —$(CH_2)_9$—.

In some embodiments, $R^2$ can be absent or selected from the group consisting of —H, —NH—, —O—, —C(═O)—, and —NH—C(═O)O—. In certain embodiments, $R^2$ can be absent. In certain embodiments, $R^2$ can be —H. In certain embodiments, $R^2$ can be —NH—. In certain embodiments, $R^2$ can be —O—. In certain embodiments, $R^2$ can be —C(═O)—. In certain embodiments, $R^2$ can be —NH—C(═O)O—.

In some embodiments, $R^3$ can be absent or selected from the group consisting of —O—, —C(═O)—, —C(═O)O—, and optionally substituted $C_1$-$C_6$ alkylene. In certain embodiments, $R^3$ can be absent. In certain embodiments, $R^3$ can be —O—. In certain embodiments, $R^3$ can be —C(═O)—. In certain embodiments, $R^3$ can be —C(═O)O—.

In certain embodiments, $R^3$ can be a $C_1$-$C_6$ alkylene. In certain embodiments, $R^3$ can be selected from the group consisting of —$CH_2$—, —$CH_2$—$CH_2$—, —$(CH_2)_3$—, —$(CH_2)_4$—, —$(CH_2)_5$—, and —$(CH_2)_6$—. In certain embodiments, $R^3$ can be —$CH_2$—. In certain embodiments, $R^3$ can be —$CH_2$—$CH_2$—. In certain embodiments, $R^3$ can be —$(CH_2)_3$—. In certain embodiments, $R^3$ can be —$(CH_2)_4$—. In certain embodiments, $R^3$ can be —$(CH_2)_5$—. In certain embodiments, $R^3$ can be —$(CH_2)_6$—.

In some embodiments, $R^4$ can be absent or selected from the group consisting of —H, —NH—, and optionally substituted $C_1$-$C_6$ alkylene. In certain embodiments, $R^4$ can be absent. In certain embodiments, $R^4$ can be —H. In certain embodiments, $R^4$ can be —NH—.

In certain embodiments, $R^4$ can be a $C_1$-$C_6$ alkylene. In some embodiments, the $R^4$ can be selected from the group consisting of —$CH_2$—, —$CH_2$—$CH_2$—, —$(CH_2)_3$—, —$(CH_2)_4$—, —$(CH_2)_5$—, and —$(CH_2)_6$—. In certain embodiments, $R^4$ can be —$CH_2$—. In certain embodiments, $R^4$ can be —$CH_2$—$CH_2$—. In certain embodiments, $R^4$ can be —$(CH_2)_3$—. In certain embodiments, $R^4$ can be —$(CH_2)_4$—. In certain embodiments, $R^4$ can be —$(CH_2)_5$—. In certain embodiments, $R^4$ can be —$(CH_2)_6$—.

In some embodiments, $R^5$ can be absent, or can be

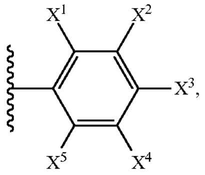

wherein $X^1$, $X^2$, $X^3$, $X^4$, and $X^5$ can each be independently selected from the group consisting of —H, —$NO_2$, —$N_3$, optionally substituted $C_2$-$C_{12}$ heterocycle, and optionally substituted $C_1$-$C_{12}$ heteroaryl.

In certain embodiments, $R^5$ can be absent. In certain embodiments, $R^5$ can be

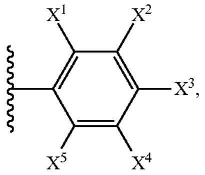

wherein $X^1$, $X^2$, $X^3$, $X^4$, and $X^5$ can each be independently selected from the group consisting of —H, —$NO_2$, —$N_3$, optionally substituted $C_2$-$C_{12}$ heterocycle, and optionally substituted $C_1$-$C_{12}$ heteroaryl. In certain embodiments, the optionally substituted $C_1$-$C_{12}$ heteroaryl can be selected from the group consisting of

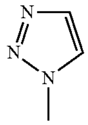 ; 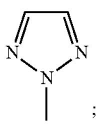 ; 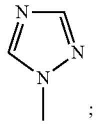 ; 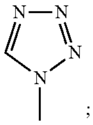 ;

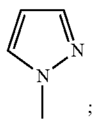 ; 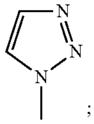 ; 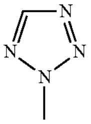 ; 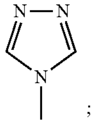 ;

-continued

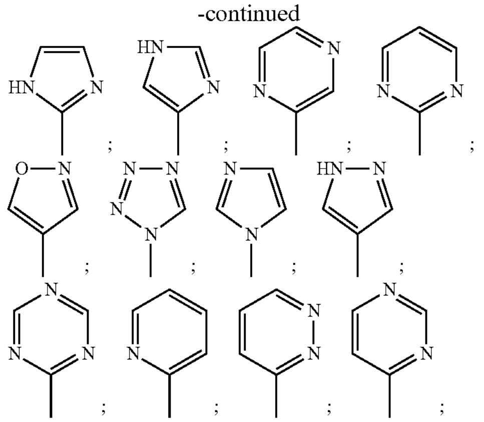

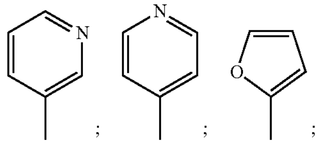 and 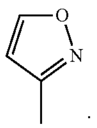

In certain embodiments, the optionally substituted $C_2$-$C_{12}$ heterocycle can be selected from the group consisting of

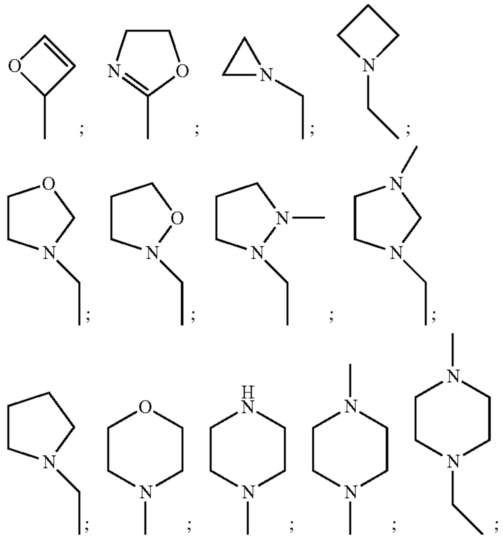

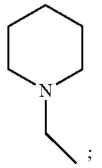 and 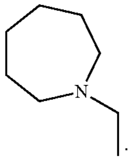

In certain embodiments, the optionally substituted $C_1$-$C_{12}$ heteroaryl can be selected from the group consisting of

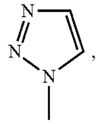, 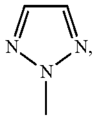 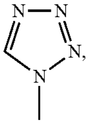 and 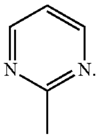

In certain embodiments, the $C_2$-$C_{12}$ heterocycle can be selected from the group consisting of

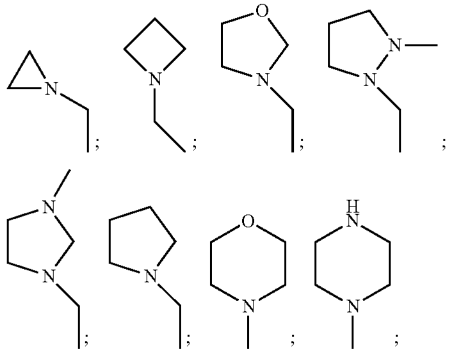

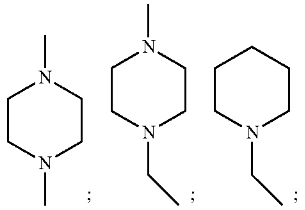 and 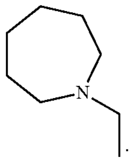

In certain embodiments, $R^5$ can be

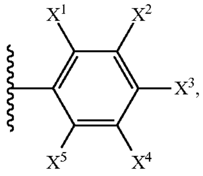

wherein $X^1$ can be —$NO_2$. In certain embodiments, $R^5$ can be

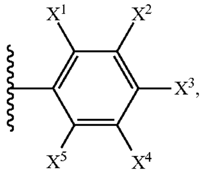

wherein $X^2$, $X^4$, and $X^5$ can each be independently —H. In certain embodiments, $R^5$ can be

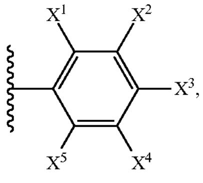

wherein $X^1$ can be —$NO_2$, $X^2$, $X^4$, and $X^5$ can each be independently —H, and $X^3$ can be —$N_3$.

In certain embodiments, $R^5$ can be

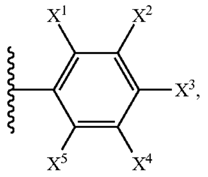

wherein $X^1$ can be —$NO_2$, $X^2$, $X^4$, and $X^5$ can each be independently —H, and $X^3$ can be

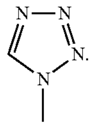

In certain embodiments, $R^5$ can be

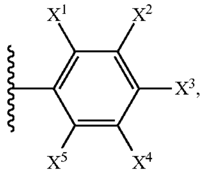

wherein $X^1$ can be —$NO_2$, $X^2$, $X^4$, and $X^5$ can each be independently —H, and $X^3$ can be

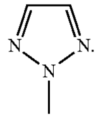

In certain embodiments, $R^5$ can be

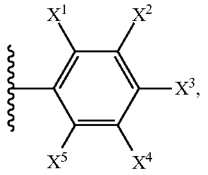

wherein $X^1$ can be —$NO_2$, $X^2$, $X^4$, and $X^5$ can each be independently —H, and $X^3$ can be

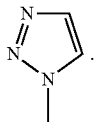

In certain embodiments, $R^5$ can be

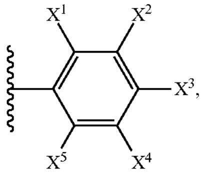

wherein $X^1$ can be —$NO_2$, $X^2$, $X^4$, and $X^5$ can each be independently —H, and $X^3$ can be

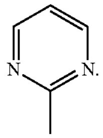

Embodiments according to Formula (I) are illustrated in Table 1. Table 1 is provided for exemplary purposes, and is not to be considered as an all-inclusive list of compounds. Additionally, while Table 1 describes the free-base embodiments of compounds 1-12, the present disclosure includes any and all appropriate pharmaceutically acceptable salts of these compounds.

TABLE 1

| Cmpd # | Structure | Name |
|---|---|---|
| 1 | 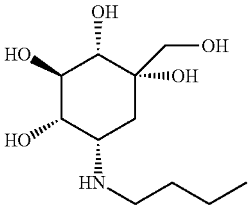 [SMILES: CCCCN[C@H]1C[C@](O)(CO)[C@@H](O)[C@H](O)[C@H]1O] | (1S,2S,3R,4S,5S)-5-(butylamino)-1-(hydroxymethyl)cyclohexane-1,2,3,4-tetraol |

TABLE 1-continued

| Cmpd # | Structure | Name |
|---|---|---|
| 2 | 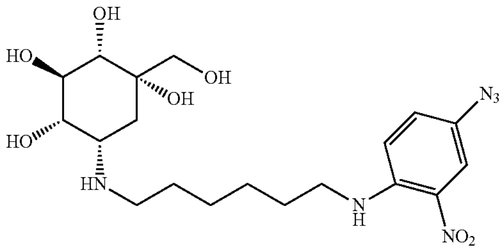 [SMILES: [N-]=[N+]=Nc1ccc(NCCCCCCN[C@H]2C[C@](O)(CO)[C@@H](O)[C@H](O)[C@H]2O)c([N+](=O)[O-])c1] | (1S,2S,3R,4S,5S)-5-((6-((4-azido-2-nitrophenyl)amino)hexyl)amino)-1-(hydroxymethyl)cyclohexane-1,2,3,4-tetraol |
| 3 | 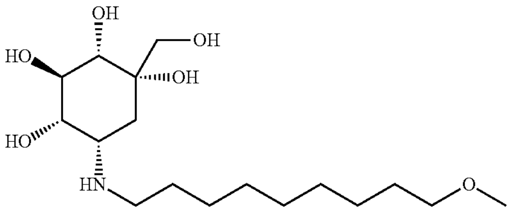 [SMILES: COCCCCCCCCCN[C@H]1C[C@](O)(CO)[C@@H](O)[C@H](O)[C@H]1O] | (1S,2S,3R,4S,5S)-1-(hydroxymethyl)-5-((9-methoxynonyl)amino)cyclohexane-1,2,3,4-tetraol |
| 4 | 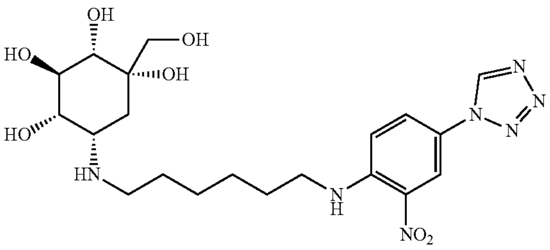 [SMILES: O=[N+]([O-])c1cc(-n2cnnn2)ccc1NCCCCCCN[C@H]1C[C@](O)(CO)[C@@H](O)[C@H](O)[C@H]1O] | (1S,2S,3R,4S,5S)-1-(hydroxymethyl)-5-((6-((2-nitro-4-(1H-tetrazol-1-yl)phenyl)amino)hexyl)amino)cyclohexane-1,2,3,4-tetraol |
| 5 | 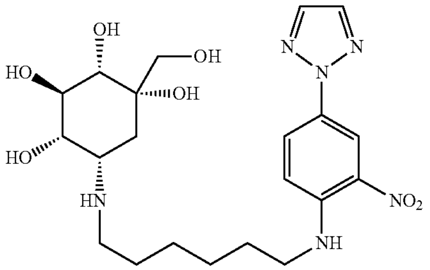 [SMILES: O=[N+]([O-])c1cc(-n2nccn2)ccc1NCCCCCCN[C@H]1C[C@](O)(CO)[C@@H](O)[C@H](O)[C@H]1O] | (1S,2S,3R,4S,5S)-1-(hydroxymethyl)-5-((6-((2-nitro-4-(2H-1,2,3-triazol-2-yl)phenyl)amino)hexyl)amino)cyclohexane-1,2,3,4-tetraol |
| 6 | 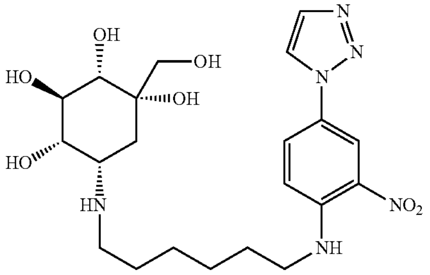 [SMILES: O=[N+]([O-])c1cc(-n2ccnn2)ccc1NCCCCCCN[C@H]1C[C@](O)(CO)[C@@H](O)[C@H](O)[C@H]1O] | (1S,2S,3R,4S,5S)-1-(hydroxymethyl)-5-((6-((2-nitro-4-(1H-1,2,3-triazol-1-yl)phenyl)amino)hexyl)amino)cyclohexane-1,2,3,4-tetraol |

TABLE 1-continued

| Cmpd # | Structure | Name |
| --- | --- | --- |
| 7 | 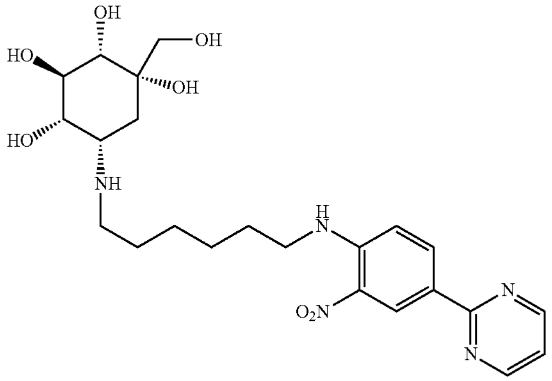 [SMILES: O=[N+]([O-])c1cc(-c2ncccn2)ccc1NCCCCCCN[C@H]1C[C@](O)(CO)[C@@H](O)[C@H](O)[C@H]1O] | (1S,2S,3R,4S,5S)-1-(hydroxymethyl)-5-((6-((2-nitro-4-(pyrimidin-2-yl)phenyl)amino)hexyl)amino)cyclohexane-1,2,3,4-tetraol |
| 8 | 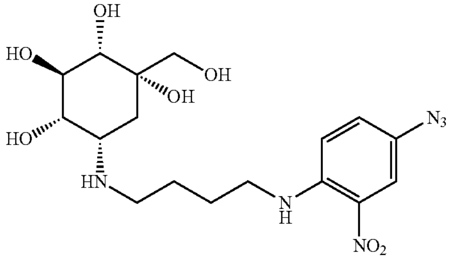 [SMILES: [N-]=[N+]=Nc1ccc(NCCCCN[C@H]2C[C@](O)(CO)[C@@H](O)[C@H](O)[C@H]2O)c([N+](=O)[O-])c1] | (1S,2S,3R,4S,5S)-5-((4-((4-azido-2-nitrophenyl)amino)butyl)amino)-1-(hydroxymethyl)cyclohexane-1,2,3,4-tetraol |
| 9 | 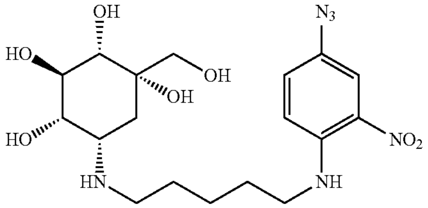 [SMILES: [N-]=[N+]=Nc1ccc(NCCCCCN[C@H]2C[C@](O)(CO)[C@@H](O)[C@H](O)[C@H]2O)c([N+](=O)[O-])c1] | (1S,2S,3R,4S,5S)-5-((5-((4-azido-2-nitrophenyl)amino)pentyl)amino)-1-(hydroxymethyl)cyclohexane-1,2,3,4-tetraol |
| 10 | 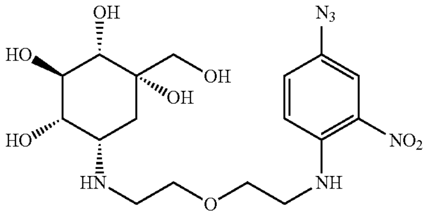 [SMILES: [N-]=[N+]=Nc1ccc(NCCOCCN[C@H]2C[C@](O)(CO)[C@@H](O)[C@H](O)[C@H]2O)c([N+](=O)[O-])c1] | (1S,2S,3R,4S,5S)-5-((2-(2-((4-azido-2-nitrophenyl)amino)ethoxy)ethyl)amino)-1-(hydroxymethyl)cyclohexane-1,2,3,4-tetraol |
| 11 | 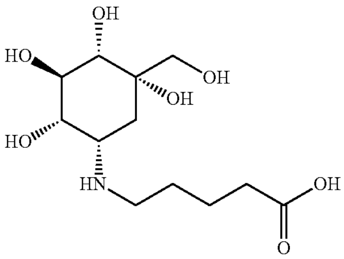 [SMILES: O=C(O)CCCCN[C@H]1C[C@](O)(CO)[C@@H](O)[C@H](O)[C@H]1O] | 5-(((1S,2S,3R,4S,5S)-2,3,4,5-tetrahydroxy-5-(hydroxymethyl)cyclohexyl)amino) pentanoic acid |

TABLE 1-continued

| Cmpd # | Structure | Name |
|---|---|---|
| 12 | 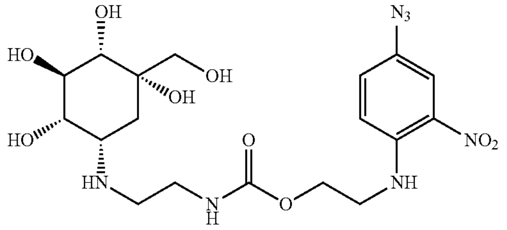 [SMILES: [N-]=[N+]=Nc1ccc(NCCOC(=O)NCCN[C@H]2C[C@](O)(CO)[C@@H](O)[C@H](O)[C@H]2O)c([N+](=O)[O-])c1] | 2-((4-azido-2-nitrophenyl)amino)ethyl (2-(((1S,2S,3R,4S,5S)-2,3,4,5-tetrahydroxy-5-(hydroxymethyl)cyclohexyl)amino)ethyl) carbamate |

In some embodiments, the compound of Formula (I) can be a compound of Formula (II):

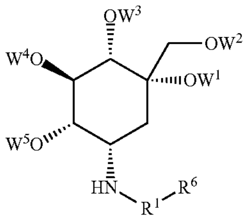

II or a pharmaceutically acceptable salt thereof, wherein $W^1$-$W^5$ are each independently selected from the group consisting of —H, —C(═O)—$C_1$-$C_9$ alkyl, and —C(═O)O—$C_1$-$C_9$ alkyl;

$R^1$ is optionally substituted $C_1$-$C_9$ alkylene;

$R^6$ is selected from the group consisting of —H, —$OR^7$, and —C(═O)—$OR^8$; wherein each of $R^7$ and $R^8$ is —H or a $C_1$-$C_6$ alkyl.

In some embodiments, $W^1$-$W^5$ can each be independently selected from the group consisting of —H, —C(═O)—$C_1$-$C_9$ alkyl, and —C(═O)O—$C_1$-$C_9$ alkyl. In some embodiments, $W^1$-$W^5$ can each be independently —C(═O)—$C_1$-$C_9$ alkyl. In some embodiments, $W^1$-$W^5$ can each be independently —C(═O)O—$C_1$-$C_9$ alkyl. In some embodiments, $W^1$-$W^5$ can each be independently —H.

In some embodiments, $R^1$ can be optionally substituted $C_1$-$C_9$ alkylene. In some embodiments, $R^1$ can be selected from the group consisting of —$CH_2$—, —$CH_2$—$CH_2$—, —$(CH_2)_3$—, —$(CH_2)_4$—, —$(CH_2)_5$—, —$(CH_2)_6$—, —$(CH_2)_7$—, —$(CH_2)_8$—, and —$(CH_2)_9$—. In certain embodiments, $R^1$ can be —$CH_2$—. In certain embodiments, le can be —$(CH_2)_2$—. In certain embodiments, $R^1$ can be —$(CH_2)_3$—. In certain embodiments, $R^1$ can be —$(CH_2)_4$—. In certain embodiments, $R^1$ can be —$(CH_2)_5$—. In certain embodiments, $R^1$ can be —$(CH_2)_6$—. In certain embodiments, $R^1$ can be —$(CH_2)_7$—. In certain embodiments, $R^1$ can be —$(CH_2)_8$—. In certain embodiments, $R^1$ can be —$(CH_2)_9$—.

In some embodiments, $R^6$ can be —H.

In some embodiments, $R^6$ can be —$OR^7$. In some embodiments, $R^7$ can —H or a $C_1$-$C_6$ alkyl. In some embodiments, $R^7$ can —H. In some embodiments, $R^7$ can be a $C_1$-$C_6$ alkyl such as methyl, ethyl, n-propyl, isopropyl, butyl, sec-butyl, t-butyl, n-pentyl, or n-hexyl. In some embodiments, the $C_1$-$C_6$ alkyl can be linear, branched, or cyclic. In certain embodiments, the $C_1$-$C_6$ alkyl is linear. In particular embodiments, the $C_1$-$C_6$ alkyl can be methyl.

In some embodiments, $R^6$ can be —C(═O)—$OR^8$. In some embodiments, $R^8$ can —H or a $C_1$-$C_6$ alkyl. In some embodiments, $R^8$ can be a $C_1$-$C_6$ alkyl such as methyl, ethyl, n-propyl, isopropyl, butyl, sec-butyl, t-butyl, n-pentyl, or n-hexyl. In some embodiments, the $C_1$-$C_6$ alkyl can be linear, branched, or cyclic. In certain embodiments, the $C_1$-$C_6$ alkyl is linear. In particular embodiments, $R^8$ can —H.

Embodiments according to Formula (II) are illustrated in Table 2. Table 2 is provided for exemplary purposes, and is not to be considered as an all-inclusive list of compounds. Additionally, while Table 2 describes the free-base embodiments of compounds 1, 3, and 11, the present disclosure includes any and all appropriate pharmaceutically acceptable salts of these compounds.

TABLE 2

| Cmpd # | Structure | Name |
|---|---|---|
| 1 | 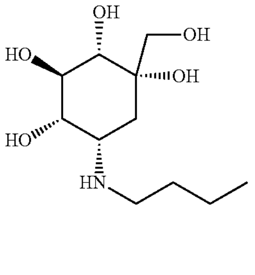 [SMILES: CCCCN[C@H]1C[C@](O)(CO)[C@@H](O)[C@H](O)[C@H]1O] | (1S,2S,3R,4S,5S)-5-(butylamino)-1-(hydroxymethyl)cyclohexane-1,2,3,4-tetraol |

TABLE 2-continued

| Cmpd # | Structure | Name |
| --- | --- | --- |
| 3 | 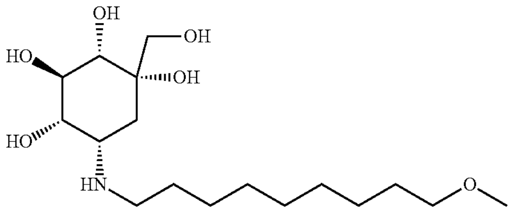 [SMILES: COCCCCCCCCCN[C@H]1C[C@](O)(CO)[C@@H](O)[C@H](O)[C@H]1O] | (1S,2S,3R,4S,5S)-1-(hydroxymethyl)-5-((9-methoxynonyl)amino)cyclohexane-1,2,3,4-tetraol |
| 11 | 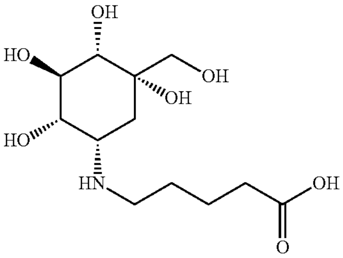 [SMILES: O=C(O)CCCCN[C@H]1C[C@](O)(CO)[C@@H](O)[C@H](O)[C@H]1O] | 5-(((1S,2S,3R,4S,5S)-2,3,4,5-tetrahydroxy-5-(hydroxymethyl)cyclohexyl)amino) pentanoic acid |

In some embodiments, the compound of Formula (I) is not a compound of Formula (II):

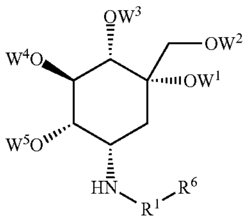

II or a pharmaceutically acceptable salt thereof, wherein $W_1$-$W_5$, $R^6$ and $R^6$ have the meanings described herein. In some embodiments, the compound of Formula I is not a compound according to Table 2, or a pharmaceutically acceptable salt thereof.

In some embodiments, the compound of Formula (I) can be a compound of Formula (III):

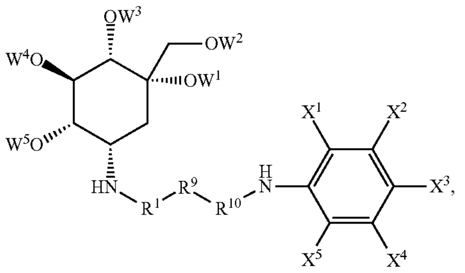

III or a pharmaceutically acceptable salt thereof, wherein $W^1$-$W^5$ are each independently selected from the group consisting of —H, —C(═O)—C1-C9 alkyl, and —C(═O)O—C1-C9 alkyl;

R1 is optionally substituted C1-C9 alkylene;

R9 is absent or selected from the group consisting of —NH—, —O—, —C(═O)—, —C(═O)O—, —NH—C(═O)—, and —NH—C(═O)O—;

R10 is absent or optionally substituted C1-C6 alkylene;

wherein X1, X2, X3, X4, and X5 are each independently selected from the group consisting of —H, —$NO_2$, —$N_3$, optionally substituted $C_2$-$C_{12}$ heterocycle, and optionally substituted $C_1$-$C_{12}$ heteroaryl.

In some embodiments, $W^1$-$W^5$ can each be independently selected from the group consisting of —H, —C(═O)—$C_1$-$C_9$ alkyl, and —C(═O)O—$C_1$-$C_9$ alkyl. In some embodiments, $W^1$-$W^5$ can each be independently —C(═O)—$C_1$-$C_9$ alkyl. In some embodiments, $W^1$-$W^5$ can each be independently —C(═O)O—$C_1$-$C_9$ alkyl. In some embodiments, $W^1$-$W^5$ can each be independently —H.

In some embodiments, le can be optionally substituted $C_1$-$C_9$ alkylene. In some embodiments, $R^1$ can be selected from the group consisting of —$CH_2$—, —$CH_2$—$CH_2$—, —$(CH_2)_3$—, —$(CH_2)_4$—, —$(CH_2)_5$—, —$(CH_2)_6$—, —$(CH_2)_7$—, —$(CH_2)_8$—, and —$(CH_2)_9$—. In certain embodiments, $R^1$ can be —$CH_2$—. In certain embodiments, $R^1$ can be —$(CH_2)_2$—. In certain embodiments, $R^1$ can be —$(CH_2)_3$—. In certain embodiments, $R^1$ can be —$(CH_2)_4$—. In certain embodiments, $R^1$ can be —$(CH_2)_5$—. In certain embodiments, $R^1$ can be —$(CH_2)_6$—. In certain embodiments, $R^1$ can be —$(CH_2)_7$—. In certain embodiments, $R^1$ can be —$(CH_2)_8$—. In certain embodiments, $R^1$ can be —$(CH_2)_9$—.

In some embodiments, $R^9$ can be absent. In some embodiments, $R^9$ can be —NH—. In some embodiments, $R^9$ can be —NH—. In some embodiments, $R^9$ can be —O—. In some embodiments, $R^9$ can be —C(═O)—. In some embodiments, $R^9$ can be —C(═O)O—. In some embodiments, $R^9$ can be —NH—C(═O)—. In some embodiments, $R^9$ can be —NH—C(═O)O—.

In some embodiments, $R^{10}$ can be absent. In some embodiments, $R^{10}$ can be optionally substituted $C_1$-$C_6$ alkylene; In some embodiments, $R^{10}$ can be selected from the group consisting of —$CH_2$—, —$CH_2$—$CH_2$—, —$(CH_2)_3$—, —$(CH_2)_4$—, —$(CH_2)_5$—, and —$(CH_2)_6$—. In certain embodiments, $R^{10}$ can be —$CH_2$—. In certain embodiments, $R^{10}$ can be —$(CH_2)_2$—. In certain embodiments, $R^{10}$ can be —$(CH_2)_3$—. In certain embodiments, $R^{10}$ can be —$(CH_2)_4$—. In certain embodiments, $R^{10}$ can be —$(CH_2)_5$—. In certain embodiments, $R^{10}$ can be —$(CH_2)_6$—.

In certain embodiments, $X^1$, $X^2$, $X^3$, $X^4$, and $X^5$ can each be independently selected from the group consisting of —H, —$NO_2$, —$N_3$, optionally substituted $C_2$-$C_{12}$ heterocycle, and optionally substituted $C_1$-$C_{12}$ heteroaryl. In certain embodiments, the optionally substituted $C_1$-$C_{12}$ heteroaryl can be selected from the group consisting of

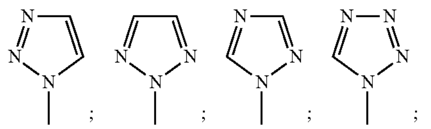

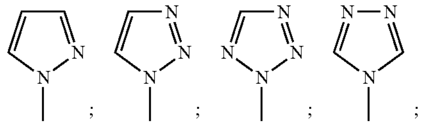

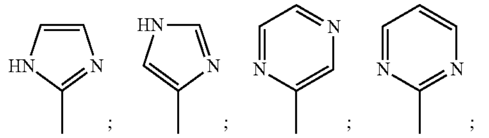

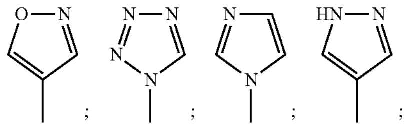

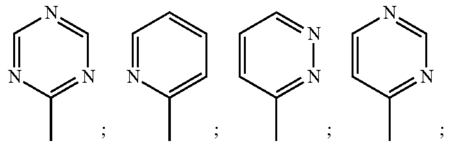

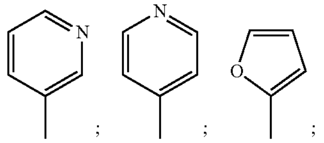

and

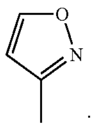

.

In certain embodiments, the optionally substituted $C_2$-$C_{12}$ heterocycle can be selected from the group consisting of

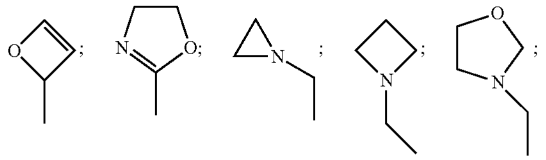

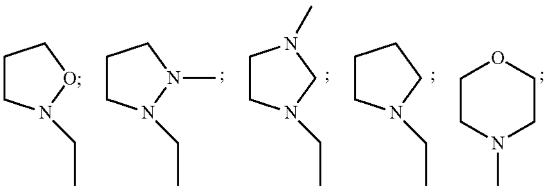

-continued

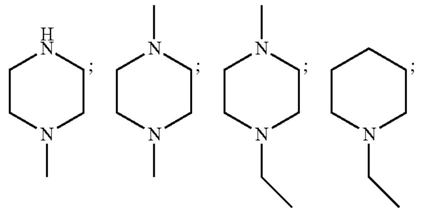

and

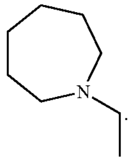

In certain embodiments, the optionally substituted $C_1$-$C_{12}$ heteroaryl can be selected from the group consisting of

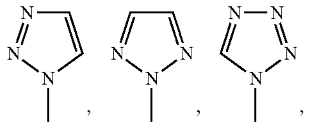

and

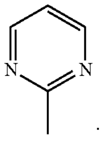

.

In certain embodiments, the optionally substituted $C_2$-$C_{12}$ heterocycle can be selected from the group consisting of

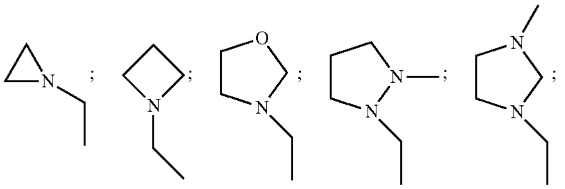

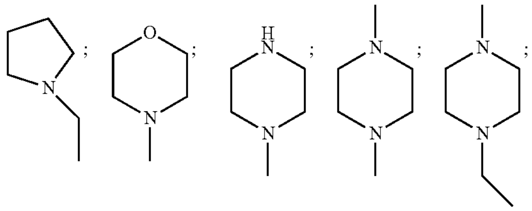

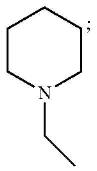

and

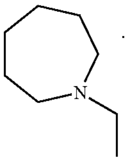

.

In certain embodiments, $X^1$ can be —$NO_2$. In certain embodiments, $X^2$, $X^4$, and $X^5$ can each be independently —H. In certain embodiments, $X^1$ can be —$NO_2$, $X^2$, $X^4$, and $X^5$ can each be independently —H, and $X^3$ can be —$N_3$.

In certain embodiments, $X^1$ can be —$NO_2$, $X^2$, $X^4$, and $X^5$ can each be independently —H, and $X^3$ can be

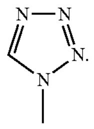

In certain embodiments, $X^1$ can be $-NO_2$, $X^2$, $X^4$, and $X^5$ can each be independently —H, and $X^3$ can be

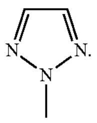

In certain embodiments, $X^1$ can be $-NO_2$, $X^2$, $X^4$, and $X^5$ can each be independently —H, and $X^3$ can be

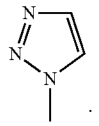

In certain embodiments, $X^1$ can be $-NO_2$, $X^2$, $X^4$, and $X^5$ can each be independently —H, and $X^3$ can be

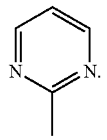

Exemplary compounds according to Formula (III) are illustrated in Table 3. Table 3 is provided for exemplary purposes, and is not to be considered as an all-inclusive list of compounds. Additionally, while Table 3 describes the free-base embodiments of compounds 2, 4, 5, 6, 7, 8, 9, 10, and 12, the present disclosure includes any and all appropriate pharmaceutically acceptable salts of these compounds.

TABLE 3

| Cmpd # | Structure | Name |
| --- | --- | --- |
| 2 | 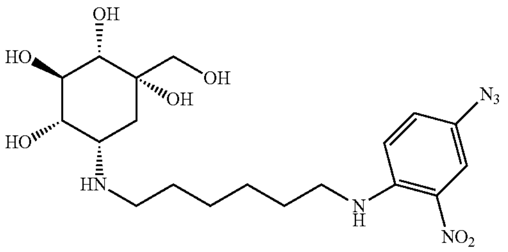 [SMILES: [N-]=[N+]=Nc1ccc(NCCCCCCN[C@H]2C[C@](O)(CO)[C@@H](O)[C@H](O)[C@H]2O)c([N+](=O)[O-])c1] | (1S,2S,3R,4S,5S)-5-((6-((4-azido-2-nitrophenyl)amino)hexyl)amino)-1-(hydroxymethyl)cyclohexane-1,2,3,4-tetraol |
| 4 | 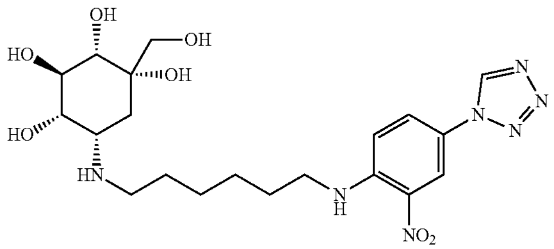 [SMILES: O=[N+]([O-])c1cc(-n2cnnn2)ccc1NCCCCCCN[C@H]1C[C@](O)(CO)[C@@H](O)[C@H](O)[C@H]1O] | (1S,2S,3R,4S,5S)-1-(hydroxymethyl)-5-((6-((2-nitro-4-(1H-tetrazol-1-yl)phenyl)amino)hexyl)amino) cyclohexane-1,2,3,4-tetraol |
| 5 | 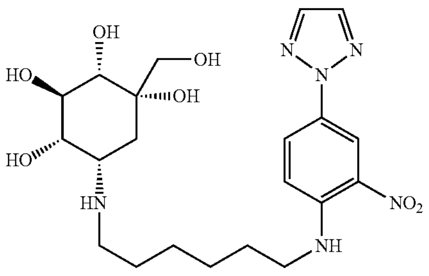 [SMILES: O=[N+]([O-])c1cc(-n2nccn2)ccc1NCCCCCCN[C@H]1C[C@](O)(CO)[C@@H](O)[C@H](O)[C@H]1O] | (1S,2S,3R,4S,5S)-1-(hydroxymethyl)-5-((6-((2-nitro-4-(2H-1,2,3-triazol-2-yl)phenyl)amino)hexyl)amino) cyclohexane-1,2,3,4-tetraol |

TABLE 3-continued

| Cmpd # | Structure | Name |
|---|---|---|
| 6 | 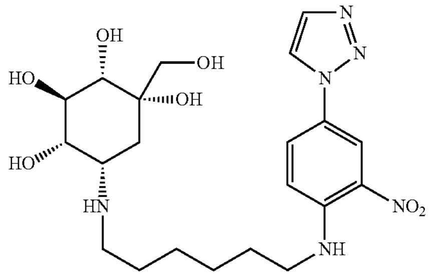 [SMILES: O=[N+]([O-])c1cc(-n2ccnn2)ccc1NCCCCCCN[C@H]1C[C@](O)(CO)[C@@H](O)[C@H](O)[C@H]1O] | (1S,2S,3R,4S,5S)-1-(hydroxymethyl)-5-((6-((2-nitro-4-(1H-1,2,3-triazol-1-yl)phenyl)amino)hexyl)amino) cyclohexane-1,2,3,4-tetraol |
| 7 | 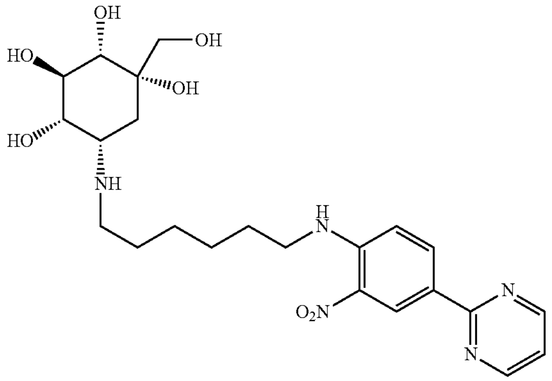 [SMILES: O=[N+]([O-])c1cc(-c2ncccn2)ccc1NCCCCCCN[C@H]1C[C@](O)(CO)[C@@H](O)[C@H](O)[C@H]1O] | (1S,2S,3R,4S,5S)-1-(hydroxymethyl)-5-((6-((2-nitro-4-(pyrimidin-2-yl)phenyl)amino)hexyl)amino) cyclohexane-1,2,3,4-tetraol |
| 8 | 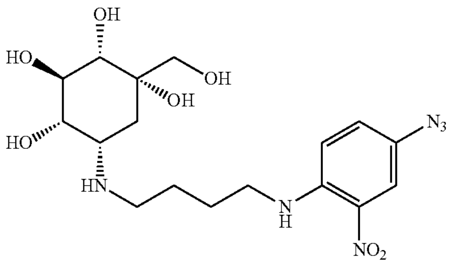 [SMILES: [N-]=[N+]=Nc1ccc(NCCCCN[C@H]2C[C@](O)(CO)[C@@H](O)[C@H](O)[C@H]2O)c([N+](=O)[O-])c1] | (1S,2S,3R,4S,5S)-5-((4-((4-azido-2-nitrophenyl)amino)butyl)amino)-1-(hydroxymethyl)cyclohexane-1,2,3,4-tetraol |
| 9 | 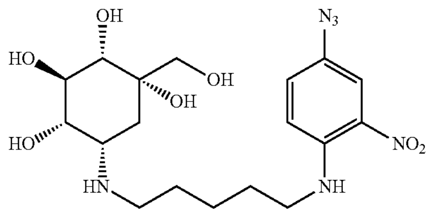 [SMILES: [N-]=[N+]=Nc1ccc(NCCCCCN[C@H]2C[C@](O)(CO)[C@@H](O)[C@H](O)[C@H]2O)c([N+](=O)[O-])c1] | (1S,2S,3R,4S,5S)-5-((5-((4-azido-2-nitrophenyl)amino)pentyl)amino)-1-(hydroxymethyl)cyclohexane-1,2,3,4-tetraol |
| 10 | 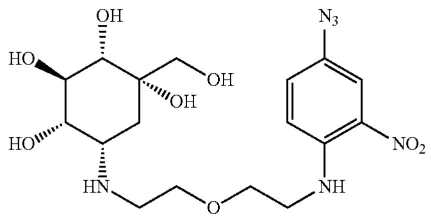 [SMILES: [N-]=[N+]=Nc1ccc(NCCOCCN[C@H]2C[C@](O)(CO)[C@@H](O)[C@H](O)[C@H]2O)c([N+](=O)[O-])c1] | (1S,2S,3R,4S,5S)-5-((2-(2-((4-azido-2-nitrophenyl)amino)ethoxy)ethyl)amino)-1-(hydroxymethyl)cyclohexane-1,2,3,4-tetraol |

TABLE 3-continued

| Cmpd # | Structure | Name |
|---|---|---|
| 12 | 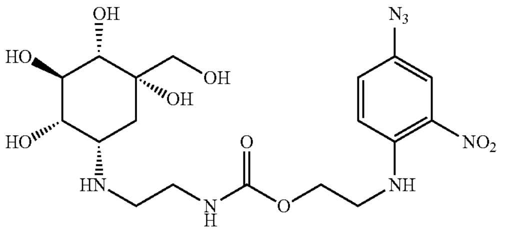 [SMILES: [N-]=[N+]=Nc1ccc(NCCOC(=O)NCCN[C@H]2C[C@](O)(CO)[C@@H](O)[C@H](O)[C@H]2O)c([N+](=O)[O-])c1] | 2-((4-azido-2-nitrophenyl)amino)ethyl (2-(((1S,2S,3R,4S,5S)-2,3,4,5-tetrahydroxy-5-(hydroxymethyl)cyclohexyl)amino)ethyl) carbamate |

In some embodiments, the compound of Formula (III) can be a compound of Formula (III-A), (III-B), or (III-C):

III-A

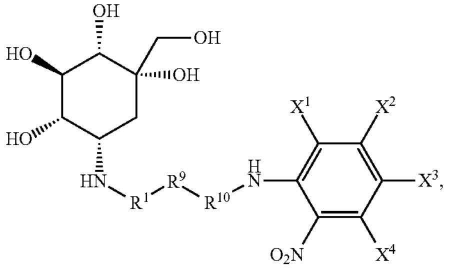

III-B

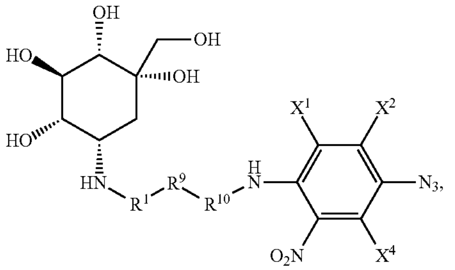

III-C

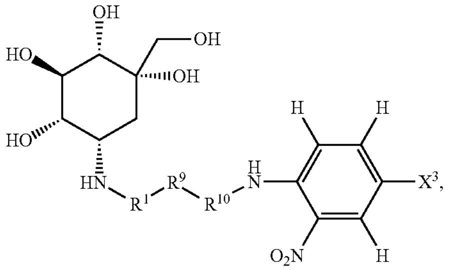

wherein $R^1$, $R^9$, $R^{10}$, $X^1$, $X^2$, $X^3$, and $X^4$ have the meanings described herein. In particular embodiments, $X^3$ can be optionally substituted $C_1$-$C_{12}$ heteroaryl. In certain embodiments, In certain embodiments, the optionally substituted $C_1$-$C_{12}$ heteroaryl can be selected from the group consisting of

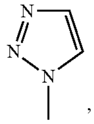 , 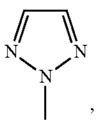 , 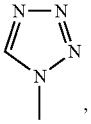 , and 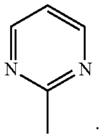 .

In some embodiments, a compound of the present disclosure can be a part of a pharmaceutical composition, which can also include one or more pharmaceutically acceptable excipients. Suitable excipients are discussed, for example, in Gennaro, A. R., Remington's Pharmaceutical Sciences, Mack Publishing Co., Easton, P.A. (18th ed, 1995), and Liberman, Hours. A. and Lachman, L, Eds., Pharmaceutical Dosage Forms, Marcel Dekker Inc., New York, N.Y. (1980).

Exemplary pharmaceutically acceptable excipients include, but are not limited to diluents, binders, fillers, buffering agents, pH modifying agents, disintegrants, dispersants, preservatives, lubricants, taste-masking agents, flavoring agents, coloring agents. The amounts and types of excipients utilized to form pharmaceutical compositions can be selected according to known principles of pharmaceutical science, as well as the desired route of administration, i.e. orally, parenterally (i.e. via subcutaneous, intravenous, intramuscular, intra-articular, intrasternal injection, or other infusion technique), bucally, sublingually, etc.

Exemplary diluents include, but are not limited to those diluents that are compressible (i.e., plastically deformable) and those that are abrasively brittle. Exemplary compressible diluents include, but are not limited to, microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, maltitol, sorbitol, xylitol, maltodextrin, trehalose, and combinations thereof. Abrasively brittle diluents include, but are not limited to, dibasic calcium phosphate (anhydrous or dihydrate), calcium phosphate tribasic, calcium carbonate, magnesium carbonate, and combinations thereof.

Exemplary binders include, but are not limited to, starches (for example, maize starch, wheat starch, rice starch, or potato starch), pregelatinized starches, gelatin, polyvinylpyrrolidone, tragacanth, polyvinyl pyrrolidone, cellulose, methylcellulose, hydroxypropylmethylcellulose, sodium carboxymethylcellulose, ethylcellulose, polyacrylamides, polyvinyloxoazolidone, polyvinylalcohols, $C_{12}C_{18}$ fatty acid alcohol, polyethylene glycol, polyols, saccharides, oligosaccharides, polypeptides, oligopeptides, and combinations thereof.

Suitable fillers include, but are not limited to, saccharides (for example, lactose, sucrose, mannitol or sorbitol), cellulose preparations, calcium phosphates (for example, tricalcium phosphate or calcium hydrogen phosphate), and combinations thereof.

Suitable buffering agents include, but are not limited to, phosphates, carbonates, citrates, tris buffers, and buffered saline salts (e.g., tris buffered saline or phosphate buffered saline) and combinations thereof, as appropriate.

Suitable pH modifiers include, but are not limited to, sodium carbonate, sodium bicarbonate, sodium citrate, citric acid, phosphoric acid, and combinations thereof.

Suitable disintegrants include, but are not limited to, non-effervescent and effervescent disintegrants. Exemplary non-effervescent disintegrants include, but are not limited to, starches such as corn starch, potato starch, pregelatinized and modified starches; sweeteners; clays such as bentonite; micro-crystalline cellulose; alginates; sodium starch glycolate; and gums such as agar, guar, locust bean, karaya, pectin, and tragacanth. Exemplary effervescent disintegrants include, but are not limited to, sodium bicarbonate in combination with citric acid, and sodium bicarbonate in combination with tartaric acid. Combinations of any of the foregoing can also be used.

Exemplary dispersants include, but are not limited to, starch, alginic acid, polyvinylpyrrolidones, guar gum, kaolin, bentonite, purified wood cellulose, sodium starch glycolate, isoamorphous silicate, microcrystalline cellulose, and combinations thereof.

Exemplary preservatives include, but are not limited to, antioxidants, such as BHA, BHT, vitamin A, vitamin C, vitamin E, retinyl palmitate, citric acid, and sodium citrate; chelators, such as EDTA, and EGTA; and antimicrobials, such as parabens, chlorobutanol, and phenol. Combinations of any of the foregoing can also be used.

Exemplary lubricants include, but are not limited to, minerals such as talc and silica; fats such as vegetable stearin, magnesium stearate, and stearic acid. Combinations of any of the foregoing can also be used.

Exemplary taste-masking agents include, but are not limited to, cellulose ethers, polyethylene glycols, polyvinyl alcohol, polyvinyl alcohol and polyethylene glycol copolymers, monoglycerides, triglycerides, acrylic polymers, mixtures of acrylic polymers and cellulose ethers, cellulose acetate phthalate, and combinations thereof.

Exemplary flavoring agents include, but are not limited to, synthetic flavor oils, flavoring aromatics, natural oils, and extracts from plants, leaves, flowers, fruits, and combinations thereof.

Exemplary coloring agents include, but are not limited to, food, drug and cosmetic colors (FD&C), drug and cosmetic colors (D&C), and external drug and cosmetic colors (Ext. D&C).

In some embodiments, the composition can be formulated into various dosage forms and administered by a number of different means that will deliver a therapeutically effective amount of the active ingredient.

In some embodiments, topical administration can involve the use of transdermal administration such as transdermal patches, or iontophoresis devices.

In some embodiments, the pharmaceutical composition can be a solid dosage forms for oral administration such as a capsule, tablet, caplet, pill, powder, pellet, or granule. In such solid dosage forms, the active ingredient can be ordinarily combined with one or more pharmaceutically acceptable excipients, examples of which are detailed above. Oral preparations can also be administered as aqueous suspensions, elixirs, or syrups. The active ingredient can be combined with various sweetening or flavoring agents, coloring agents, emulsifying and/or suspending agents, and diluents such as water, ethanol, glycerin, and combinations thereof. For administration by inhalation, the compounds can be delivered in the form of an aerosol spray from pressured container, or dispenser which contains a suitable propellant, e.g., a gas such as carbon dioxide, or a nebulizer.

In some embodiments, the preparation can be an aqueous or an oil-based solution for parenteral administration. The parenteral administration can be subcutaneous, intradermal, intravenous, intramuscular, intra-articular, or intraperitoneal. Aqueous solutions can include a sterile diluent such as water, saline solution, a pharmaceutically acceptable polyol such as glycerol and propylene glycol, and other synthetic solvents; an antibacterial and/or antifungal agent such as benzyl alcohol, methyl paraben, chlorobutanol, phenol, thimerosal, and the like; an antioxidant such as ascorbic acid and sodium bisulfate; a chelating agent such as ethylenediaminetetraacetic acid; a buffer such as acetate, citrate, and phosphate; and/or an agent for the adjustment of tonicity such as sodium chloride, dextrose, and a polyalcohol such as mannitol and sorbitol. The pH of the aqueous solution can be adjusted with acids or bases such as hydrochloric acid or sodium hydroxide. Oil-based solutions or suspensions can further comprise sesame, peanut, olive oil, and mineral oil. The compositions can be presented in unit-dose or multi-dose containers, such as sealed ampoules and vials, and can be stored in a freeze-dried (lyophilized) condition, which requires the addition of the sterile liquid carried, such as water for injections, immediately prior to use. Extemporaneous injection solutions and suspensions can be prepared from sterile powders, granules, or tablets.

In some embodiments, penetrants appropriate to the barrier to be permeated can be generally included in the preparation for topical (e.g., transdermal or transmucosal) administration. Pharmaceutical compositions adapted for topical administration can be formulated as ointments, creams, suspensions, lotions, powders, solutions, pastes, gels, sprays, aerosols, or oils. In some embodiments, the pharmaceutical composition can be applied as a topical ointment or cream. When formulated in an ointment, the active ingredient can be employed with either a paraffinic or a water-miscible ointment base. Alternatively, the active ingredient can be formulated in a cream with an oil-in-water cream base or a water-in-oil base. Pharmaceutical compositions adapted for topical administration to the eye include eye drops, wherein the active ingredient can be dissolved or suspended in a suitable carrier, especially an aqueous solvent. Pharmaceutical compositions adapted for topical administration in the mouth include lozenges, pastilles, and mouth washes. Transmucosal administration can be accomplished through the use of nasal sprays, aerosol sprays, tablets, or suppositories. Transdermal administration can be accomplished through the use of ointments, salves, gels, patches, or creams.

In some embodiments, subjects can be, but is not limited to, a human, and/or a companion animal such as a cat, dog, rodent, or horse; a research animal such as a rabbit, sheep, pig, dog, non-human primate (such as chimpanzees, monkeys, and gorillas), mouse, rat or other rodent; an agricultural animal such as a cow, pig, goat, deer, chicken or other fowl; and a zoo animal; The subject can be of any age without limitation. In some embodiments, the subject can be a human.

In some embodiments, a compound of the present disclosure can be administered in a therapeutically effective amount, either on its own, or formulated as a composition, which includes prophylactic amounts or lower dosages, for example, when combined with another agent. As used herein, "an effective amount" refers to doses of compound sufficient to provide circulating concentrations high enough to impart a beneficial effect on the recipient thereof. The precise amount to be administered can be determined by the skilled practitioner in view of desired dosages, side effects, and medical history of the patient.

In some embodiments, dosage levels of active ingredients in the pharmaceutical compositions can vary so as to administer an amount of the active compound(s) that can be effective to achieve the desired therapeutic response for a particular patient.

In some embodiments, the selected dose level can depend on the activity of the compound of the present disclosure, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose can be divided into multiple doses for purposes of administration, for example, two to four doses per day. It will be understood, however, that the specific dose level for any particular patient can depend on a variety of factors, including the body weight, general health, diet, time and route of administration and combination with other therapeutic agents and the severity of the condition or disease being treated. The adult human daily dosage can range from between about 1 mg to about 1 g, or from between about 10 mg and 100 mg, of the compound of the present disclosure per 10 kilogram body weight. In some embodiments, a total daily dose can be from 0.1 mg/kg body weight to 100 mg/kg body weight, or from 1 mg/kg body weight to 60 mg/kg body weight, or from 2 mg/kg body weight to 50 mg/kg body weight, or from 3 mg/kg body weight to 30 mg/kg body weight. The daily dose can be administered over one or more administering events over day. In some embodiments, the daily dose can be distributed over two administering events per day (BID), three administering events per day (TID), or four administering events per day (QID). In some embodiments, a single administering event dose ranging from 1 mg/kg body weight to 10 mg/kg body weight is administered BID to a human making a total daily dose from 2 mg/kg body weight to 20 mg/kg body weight. In some embodiments, a single administering event dose ranging from 1 mg/kg body weight to 10 mg/kg body weight is administered TID to a human making a total daily dose from 3 mg/kg body weight to 30 mg/kg body weight. In some embodiments, the amounts of compounds of present disclosure which can be administered to a cell or animal can depend upon numerous factors well understood by one of skill in the art, such as the molecular weights of compounds of present disclosure, and the routes of administration.

In some embodiments, a compound of the present disclosure can be used for treating a number of diseases or conditions for which inhibiting glucosidases is beneficial. Glucosidases are a class of enzymes involved in breaking down complex carbohydrates such as starch and glycogen into their respective monomers. Glucosidases include alpha-amylase, beta-amylase, gamma-amylase, cellulase, sucrase-isomaltase, mannosyl-oligosaccharide glucosidase, alpha-glucosidase, beta-glucosidase, lactase, debranching enzyme, and pullulanase. Alpha-glucosidases include maltase, glucoinvertase, glucosidosucrase, maltase-glucoamylase, alpha-glucopyranosidase, glucosidoinvertase, alpha-D-glucosidase, alpha-glucoside hydrolase, alpha-1,4-glucosidase, and alpha-D-glucoside glycohydrolase.

Exemplary diseases or conditions that can be treated with the compounds and compositions thereof disclosed herein include diabetes, diabetes mellitus type 2, hepatitis C virus (HCV) infection, hepatitis B virus (HBV) infection, dengue virus (DENV) infection, Marburg virus (MARV) infection, Ebola virus (EBOV) infection, BVHV, human immunodeficiency virus (HIV) infection, influenza A infection, influenza B infection, encephalitis virus infection (including, for example, eastern equine encephalitis virus infection (EEEV), western equine encephalitis virus infection (WEEV), Venezuelan equine encephalitis virus infection (VEEV), and Japanese encephalitis virus (JEV) infection), Zika virus infection, yellow fever virus (YFV) infection, Pompe disease, maltase-glucoamylase deficiency, Gaucher disease, mumps, acute pancreatitis, macroamylasemia, sucrase-isolmaltase deficiency, MOGS-CDG, celiac disease, Crohn's disease, and Cori's disease.

In some embodiments, the compounds of the present disclosure can be used for treating a number of diseases or conditions, for which inhibiting ceramide glucosyltransferase and/or lowering a glycosphingolipid concentration is beneficial. Examples of such diseases or conditions include, but are not limited to, Gaucher disease (including Type I, Type II and Type III Gaucher disease), Fabry disease, Sandhoff disease, Tay-Sachs disease, Parkinson's disease, type II diabetes, hypertrophy or hyperplasia associated with diabetic nephropathy, an elevated blood glucose level, and an elevated glycated hemoglobin level, a glomerular disease, and lupus such as systemic lupus erythematosus. Examples of the glomerular disease include, but are not limited to, mesangial proliferative glomerulonephritis, collapsing glomerulopathy, proliferative lupus nephritis, crescentic glomerulonephritis, and membranous nephropathy.

In some embodiments, miglustat can work as a chaperon for mutated acid beta-glucosidase in cells with Gaucher disease mutations. Thus, the compounds of the present disclosure can be used as chaperones.

In some embodiments, a disease or condition, for which inhibiting ceramide glucosyltransferase and/or lowering a glycosphingolipid concentration is beneficial, can be a lysosomal glycosphinglipid storage disease (LSD), such as Gaucher (types I, II and III) disease, Fabry disease, Sandhoff disease, Tay-Sachs disease, GM1 Gangliosidosis, and Niemann-Pick Type C disease.

In some embodiments, a disease or condition, for which inhibiting ceramide glucosyltransferase and/or lowering a glycosphingolipid concentration is beneficial, can be multiple myeloma.

In some embodiments, inhibition of osteoclastogenesis and/or reducing osteoclast activation associated with multiple myeloma with an agent, can be accomplished using one or more of the compounds disclosed herein. In some embodiments, a disease or condition, for which inhibiting ceramide glucosyltransferase and/or lowering a glycosphingolipid concentration is beneficial, can be osteoporosis or osteoarthritis. In some embodiments, inhibition of osteoclastogenesis and/or reducing osteoclast activation associated with these disorders can prevent bone resorption.

In some embodiments, a disease or condition, for which inhibiting ceramide glucosyltransferase and/or lowering a glycosphingolipid concentration is beneficial, can be polycystic kidney disease, such as an autosomal dominant and recessive form of the polycyctic kidney disease. In some embodiments, a disease or condition, for which inhibiting ceramide glucosyltransferase and/or lowering a glycosphingolipid concentration is beneficial, can treat atherosclerosis or renal hypertrophy in a diabetic patient.

In some embodiments, a disease or condition, for which inhibiting ceramide glucosyltransferase and/or lowering a glycosphingolipid concentration is beneficial, can be Type II diabetes, or its related disease or condition. In some embodiments, such disease or condition can be a non-alcoholic fatty liver disease, which can be a consequence of the metabolic syndrome and type II diabetes. In some embodiments, the related disease or condition can be a metabolic syndrome or associated dyslipidemia, which can be a precursor of type II diabetes or atherosclerosis. In some embodiments, the compounds of the present disclosure can be used prophylactically for the prevention of Type II diabetes and/or its related disease or condition.

Without wishing to be bound by a particular theory, the rationale for treating or preventing Type II diabetes and/or its related disease or condition is that compounds of the present disclosure reduce the concentration of glucosylceramide, and can therefore also reduce the expression of gangliosides. Expression of gangliosides, especially GM3, can result in the engagement of insulin receptor into lipid rafts, and cause receptor inactivation and internalization, which results in insulin resistance. Again, without wishing to be bound by a particular theory, it is believed that the compounds of the present disclosure can deplete cellular surfaces of GM3 and sensitize the cells to insulin, thereby being useful in the treatment of insulin resistance. As is well appreciated in the art, insulin resistance can lead to the development of metabolic syndrome, type II diabetes, non-alcoholic liver disease, and atherosclerosis.

In some embodiments, the compounds of the present disclosure can be used for the treatment of a bacterial diseases caused by a toxin, which binds through or to glycosphingolipid or ganglioside. For example, cholera is caused by a toxin (cholera toxin) that binds via its B-subunit to ganglioside GM1. By oral iminosugar treatment of a cholera patient, or by iminosugar treatment of colonic irrigation, the expression of the GM1 target by susceptible cells in the gut epithelium can be abolished or substantially reduced, and have a corresponding therapeutic effect by reducing the effect of the toxin. Another disease involving bacterial toxins can be postdiarrhea hemolytic uremic syndrome, which is commonly associated with particular strains of *E. coli* bacteria that produce Shiga toxin type-2, which binds to the ganglioside globotriaosylceramide (Gb3). By analogy to the scenario described for cholera therapy, the iminosugars can be used to treat *E. coli* associated disorders by reducing cellular expression of the ganglioside target of the toxin, such as Gb3. Shiga toxin-2 can be commonly expressed by *E. coli* 0157:H7 which is a strain of *E. coli* known to cause enterohemorrhagic disease. The iminosugars can be used therefore to treat enterohemorrhagic disease associated with 0157, and enterohemorrhagic disease caused by other bacteria that express Shiga toxin-2.

In some embodiments, a compound of the present disclosure, such as a compound of Formula (I), Formula (II), Formula (III), Formula (III-A), Formula (III-B), or Formula (III-C), can be administered with one or more additional anti-diabetic drugs.

In some embodiments, a compound of the present disclosure can be administered to an animal in need thereof. Compounds of the present disclosure can inhibit glycosidase function, or they can treat the individual. In one embodiment the treatment can include reducing blood sugar in the animal. Another embodiment includes a method of treating Gaucher's disease and Pompe disease.

In some embodiments, the animal, to whom a compound of the present disclosure can be administered, can be an animal having diabetes, such as a mammal, including, but not limited to, a rodent or a primate, such as a human.

In some embodiments, the amount of a compound of the present disclosure, administered to an animal or to an animal cell to the methods of the invention can be an amount effective to inhibit the glycosidase function. The term "inhibit" as used herein can refer to the detectable reduction and/or elimination of a biological activity exhibited in the absence of a compound of the present disclosure. The term "effective amount" can refer to that amount of any of the compounds described herein necessary to achieve the indicated effect. The term "treatment" as used herein can refer to reducing or alleviating symptoms in a subject, preventing symptoms from worsening or progressing, inhibition or elimination of the causative agent, or prevention of diabetes in a subject who is free therefrom.

In some embodiments, the animal, to whom a compound of the present disclosure can be administered, can be an animal having Type I diabetes, such as a mammal, including, but not limited to, a rodent or a primate, such as a human.

In some embodiments, the animal, to whom a compound of the present disclosure can be administered, can be an animal having Type 2 diabetes, such as a mammal, including, but not limited to, a rodent or a primate, such as a human.

In some embodiment, the animal to whom a compound of the presence disclosure can be administered can be an animal infected with HCV.

In some embodiment, the animal to whom a compound of the presence disclosure can be administered can be an animal infected with HBV.

In some embodiment, the animal to whom a compound of the presence disclosure can be administered can be an animal infected with DENY.

In some embodiment, the animal to whom a compound of the presence disclosure can be administered can be an animal infected with MARV.

In some embodiment, the animal to whom a compound of the presence disclosure can be administered can be an animal infected with EBOV.

In some embodiment, the animal to whom a compound of the presence disclosure can be administered can be an animal infected with BVHV.

In some embodiment, the animal to whom a compound of the presence disclosure can be administered can be an animal infected with HIV.

In some embodiment, the animal to whom a compound of the presence disclosure can be administered can be an animal infected with influenza. In certain embodiments, the influenza can be an influenza A infection or an influenza B infection.

In some embodiment, the animal to whom a compound of the presence disclosure can be administered can be an animal infected with an encephalitis virus, such as western equine encephalitis virus, eastern equine encephalitis virus, Venezuelan equine encephalitis virus, or Japanese encephalitis virus.

In some embodiment, the animal to whom a compound of the presence disclosure can be administered can be an animal infected with Zika virus.

In some embodiment, the animal to whom a compound of the presence disclosure can be administered can be an animal infected with YFV.

The embodiments discussed herein will be further clarified in the following examples. It should be understood that these examples are not limiting to the embodiments described above.

EXAMPLES

The following Examples are included to demonstrate various aspects of the present disclosure. However, those of skill in the art should, in light of the present disclosure, appreciate that many changes can be made in the specific Example which are disclosed and still obtain a like or similar result without departing from the spirit and scope of the disclosure.

For all chemical scheme Examples given below, intermediate and product identity was confirmed by proton nuclear magnetic resonance spectroscopy ($^1$H-NMR) and/or liquid chromatography—mass spectrometry (LCMS). Product purity was confirmed by LCMS and high performance liquid chromatography (HPLC) with a target purity of ≥ approximately 90%. Purity of intermediates was suitable for the intended use. In selected cases (e.g. where the intermediate was considered likely to be labile or where subsequent purification was expected to provide suitable material), the intermediate after workup was moved forward to the next reaction without further purification. References to purification on silica, by column, or by chromatography, unless otherwise specified refer to purification by column chromatography using silica gel (100-200 mesh unless otherwise specified) with the indicated eluent. References to evaporation, or removal or concentration of reaction or volatiles or solvent, unless otherwise specified refer to solvent removal under reduced pressure using a diaphragm vacuum pump and ROTAVAPOR system. References to purification by preparative HPLC unless otherwise specified indicate a KINETEX Evo reverse phase C18 column (5 μm, 250 mm×21.2 mm), with an acetonitrile-water slow gradient and 5 mM ammonium bicarbonate buffer. For some intermediates and products more than one batch was prepared and combined where necessary to provide the desired amounts. Molar equivalents to that of the principal reactant are shown as eq. Reaction endpoints were determined by thin layer chromatography on silica. The Examples below provide representative conditions and scales for single batches. Weights of intermediates and products are approximate. Room temperature (RT) is approximately 20° C. to 35° C.

Example 1: Synthesis of (1S,2S,3R,4S,5S)-5-(butylamino)-1-(hydroxymethyl)cyclohexane-1,2,3,4-tetraol (Compound 1)

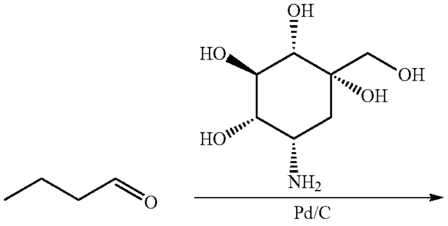

-continued

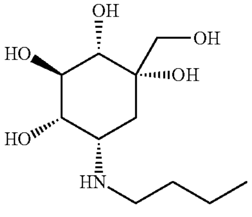

1

Preparation of Compound 1: Butyraldehyde (200 mg, 2.70 eq) in MeOH (15 mL) was reacted with valiolamine (1.2 eq), a catalytic amount of acetic acid (AcOH), and 10% Pd/C (100 mg), under hydrogen at balloon pressure, at room temperature for 16 hr. The reaction mixture was filtered, and the filtrate was concentrated. Preparative HPLC purification afforded 60 mg of Compound 1 as colorless thick syrup. Proton NMR (500 MHz, $CD_3OD$): δ 3.79-3.75 (m, 1H), 3.60-3.51 (m, 2H), 3.37-3.35 (m, 2H), 3.30-3.21 (m, 1H), 2.99-2.94 (m, 1H), 2.69-2.63 (m, 1H), 2.08-2.03 (m, 1H), 1.62-1.55 (m, 3H), 1.42-1.35 (m, 2H), 0.89 (t, 3H). Calculated Mass: 249.31. Observed Mass: 250.2 (M+H).

Example 2: Synthesis of (1S,2S,3R,4S,5S)-5-((6-((4-azido-2-nitrophenyl)amino)hexyl)amino)-1-(hydroxymethyl)cyclohexane-1,2,3,4-tetraol (Compound 2)

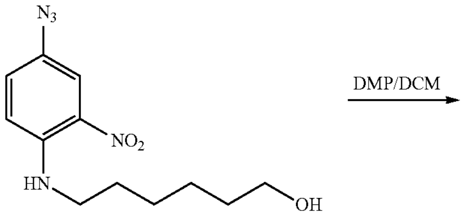

2.1

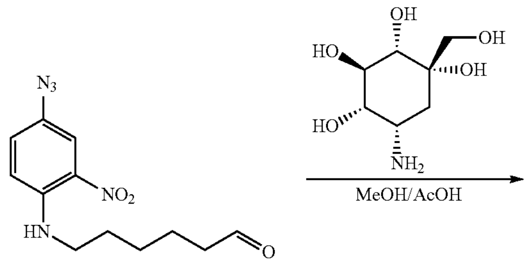

2.2

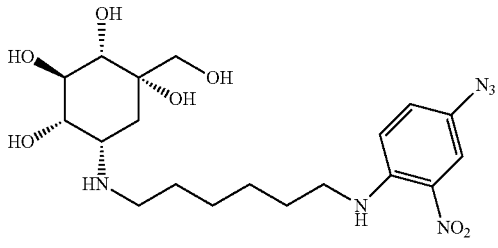

2

Compound 2.1 can be prepared according to the procedure described in U.S. Pat. No. 8,975,280, the entirety of which is hereby incorporated by reference.

Preparation of 2.2: 2.1 (500 mg, 1.79 mmol) in dichloromethane (DCM, 20 mL) was reacted with Dess Martin Periodinane (DMP, 1.2 eq) at 0° C. The reaction mixture was raised to RT for 2 hr. The reaction was diluted with DCM (20 mL) and washed with saturated sodium bicarbonate ($NaHCO_3$) solution. The organic layer was dried over anhydrous sodium sulfate ($Na_2SO_4$), filtered, concentrated, and purified by column chromatography (20% ethyl acetate (EtOAc)/hexane) to afford 350 mg of 2.2.

Preparation of Compound 2: 2.2 (300 mg, 1.00 mmol) in methanol (MeOH, 10 mL) was reacted with valiolamine (0.8 eq), catalytic AcOH, and sodium cyanoborohydride ($NaCNBH_3$, 1.5 eq) at RT for 16 hr. The volatiles were removed and preparative HPLC purification afforded 106 mg of Compound 2. Proton NMR (400 MHz, $CD_3OD$): δ7.80 (d, J=2.7 Hz, 1H), 7.26 (dd, J=9.2, 2.8 Hz, 1H), 7.09 (d, J=9.2 Hz, 1H), 3.75-3.67 (m, 1H), 3.57-3.48 (m, 2H), 3.40-3.37 (m, 2H), 3.36 (t, J=1.6 Hz, 1H), 3.12-3.06 (m, 1H), 2.85-2.77 (m, 1H), 2.57-2.45 (m, 1H), 2.01 (dd, J=15.0, 3.2 Hz, 1H), 1.78-1.69 (m, 2H), 1.62-1.39 (m, 8H). Calculated Mass: 454.4. Observed Mass: 455.4 (M+H).

Example 3: Synthesis of (1S,2S,3R,4S,5S)-1-(hydroxymethyl)-5-((9-methoxynonyl)amino)cyclohexane-1,2,3,4-tetraol (Compound 3)

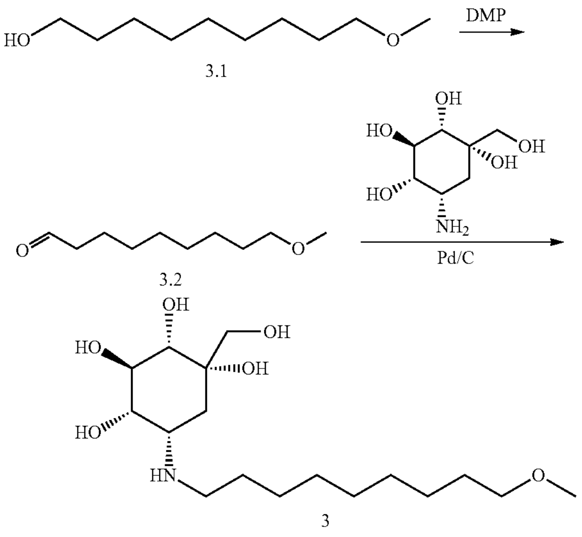

3.1

3.2

3

Methoxynonanol (3.1) can be prepared for example as shown in WO2010096764.

Preparation of 3.2: 3.1 (400 mg, 2.20 mmol) in DCM (25 mL) was mixed with DMP (1.2 eq) at 0° C., then raised to RT and reacted for 4 hr. The reaction was filtered through a celite bed and the filtrate was concentrated. The material was purified by silica gel chromatography (20% EtOAc/hexane) to afford 300 mg of 3.2.

Preparation of Compound 3: 3.2 (300 mg, 1.70 eq) in MeOH (20 mL) was reacted with valiolamine (1.2 eq), catalytic AcOH, and 10% Pd/C (150 mg), under hydrogen gas at balloon pressure, at RT for 16 hr. The reaction was filtered and the filtrate was concentrated. Preparative HPLC purification gave 100 mg of Compound 3 as thick syrup. Proton NMR (500 MHz, $CD_3OD$): δ 3.75 (t, 1H), 3.59-3.51 (m, 2H), 3.39-3.35 (m, 4H), 3.34-3.31 (m, 4H), 3.10-3.05 (m, 1H), 2.80-2.75 (m, 1H), 2.71-2.65 (m, 1H), 2.01 (dd, 1H), 1.49-1.41 (m, 5H), 1.39-1.31 (m, 9H). Calculated Mass: 349.4. Observed Mass: 350.3 (M+H).

Example 4: Synthesis of (1S,2S,3R,4S,5S)-1-(hydroxymethyl)-5-((6-((2-nitro-4-(1H-tetrazol-1-yl)phenyl)amino)hexyl)amino)cyclohexane-1,2,3,4-tetraol (Compound 4)

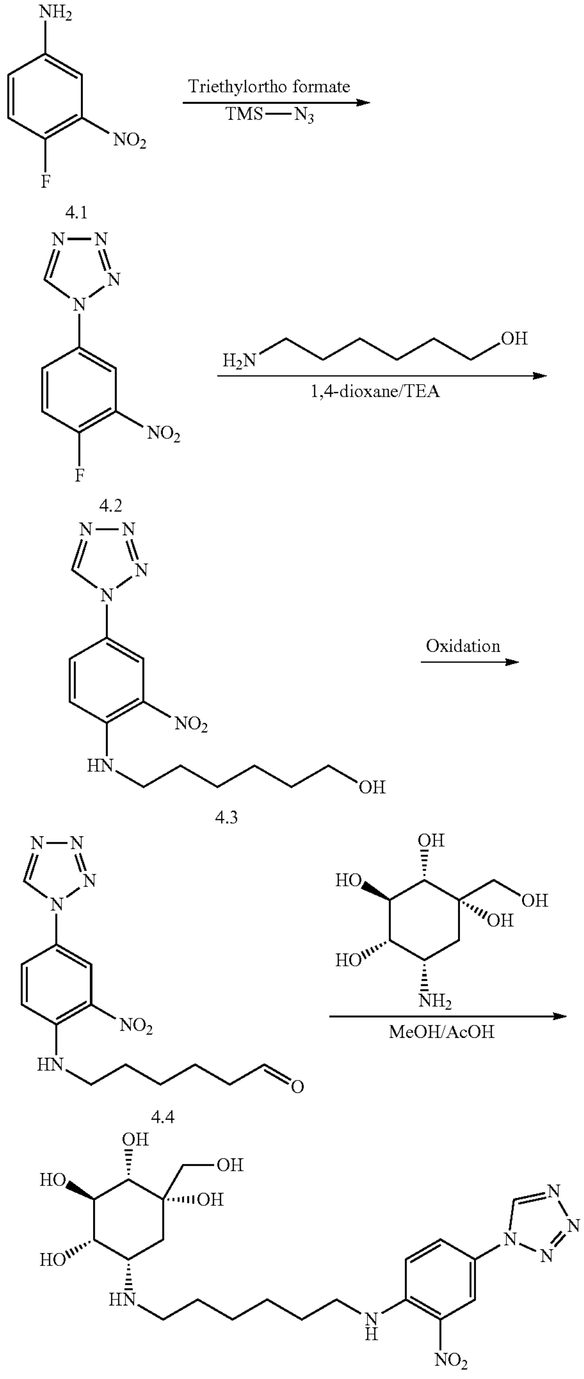

4.1

4.2

4.3

4.4

4

Preparation of 4.2: 4.1 (1.0 g, 6.41 mmol) in acetic acid (20 mL) was mixed with triethylorthoformate (5.0 eq) at 0° C., raised to RT for 30 min, cooled and added with trimethylsilyl azide (TMS-N3) (5.0 eq) at 0° C. The reaction mixture was raised to 80° C. for 4 hr and was concentrated. The residue was diluted with ice-cold water (20 mL) and extracted with EtOAc (2×20 mL). The combined organic layer was washed with water (2×10 mL), dried over anhydrous $Na_2SO_4$, filtered, and concentrated. The material was purified by silica gel column chromatography (60-120 mesh silica gel) eluting with 20-30% EtOAc/hexane to afford 900 mg of 4.2.

Preparation of 4.3: 4.2 (1.1 g, 5.26 mmol) in 1,4-dioxane (20 mL) was mixed with triethylamine (TEA, 3.0 eq) and aminohexanol (1.2 eq) at RT and was raised to 80° C. for 16 hr. The reaction was concentrated, and the residue was diluted with ice-cold water (30 mL) and extracted with EtOAc (2×50 mL). The combined organic layer was dried over anhydrous $Na_2SO_4$, filtered, and concentrated. The material was purified by silica gel column chromatography (60-120 mesh silica gel) eluting with 50-100% EtOAc/hexane to afford 1 g of 4.3.

Preparation of 4.4: Oxalylchloride (2.0 eq) in DCM (15 mL) was mixed with dimethyl sulfoxide (DMSO, 4 eq), cooled to −78° C. for 10 min, added with 4.3 (500 mg, 1.63 mmol), and reacted at 78° C. for 20 min. The reaction mixture was quenched with TEA (5.4 eq) at −78° C. for 1 hr, then stirred at RT for 2 hr. Reaction was diluted with ice-cold water and extracted with DCM (2×25 mL). The combined organic layer was dried over $Na_2SO_4$, filtered and concentrated. The material was purified by silica gel column chromatography (10% EtOAc/hexane) to afford 300 mg of 4.4.

Preparation of Compound 4: 4.4 (300 mg, 1.00 mmol) in MeOH (10 mL) was reacted with valiolamine (0.8 eq), catalytic AcOH, and $NaCNBH_3$ (1.5 eq) at RT for 16 hr. Volatiles were removed. Preparative HPLC purification afforded 60 mg of Compound 4 as yellow thick syrup. Proton NMR (500 MHz, $CD_3OD$): δ 9.75 (s, 1H), 8.62 (d, 1H), 7.99-7.90 (m, 1H), 7.25 (d, 1H), 3.79-3.75 (m, 2H), 3.59-3.49 (m, 4H), 3.39-3.35 (m, 2H), 3.10-3.05 (m, 1H), 2.80-2.75 (m, 1.6H), 2.71-2.65 (m, 1.4H), 2.01 (dd, 1H), 1.82-1.75 (m, 2H), 1.61-1.43 (m, 6H). Calculated Mass: 481.5. Observed Mass: 482.4 (M+H).

Example 5: Synthesis of (1S,2S,3R,4S,5S)-1-(hydroxymethyl)-5-((6-((2-nitro-4-(2H-1,2,3-triazol-2-yl)phenyl)amino)hexyl)amino)cyclohexane-1,2,3,4-tetraol (Compound 5)

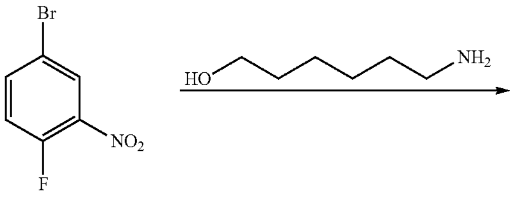

5.1

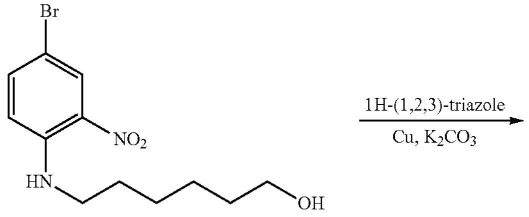

5.2

-continued

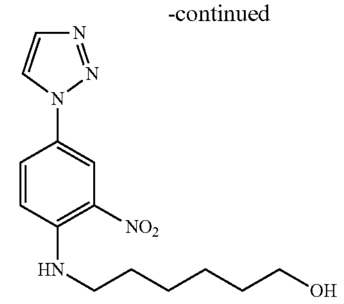

5.3a and

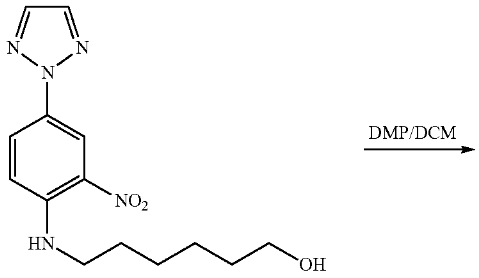

5.3b

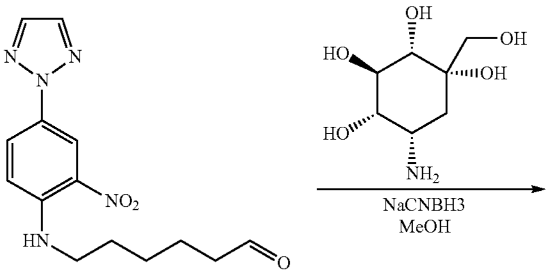

5.4b

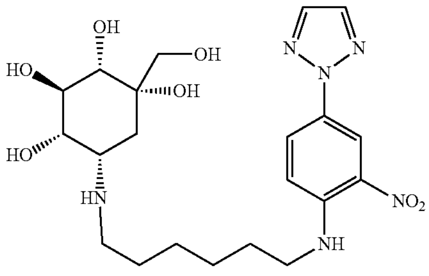

5

Preparation of 5.2: 4-Bromo-1-fluoro-2-nitrobenzene (10 g, 45.45 mmol) in 1,4-dioxane (60 mL) was mixed with TEA (3.0 eq) and aminohexanol (1.5 eq) at RT. The reaction mixture was raised to 60° C. and reacted for 16 hr. Volatiles were removed and the obtained material was purified by silica gel flash column chromatography (35% EtOAc/hexane) to afford 12 g of 5.2 as orange red solid.

Preparation of 5.3a and 5.3b: 5.2 (5 g, 15.70 mmol) was mixed with 1H-1,2,3-triazole (8.5 eq), Cu (2.1 eq), and $K_2CO_3$ (1.7 eq) at RT, and raised to 160° C. for 24 hr. Reaction mixture was diluted and mixed with 100 mL EtOAc. The organic layer was separated and concentrated. The mixture of products was purified by silica gel flash column chromatography (30% EtOAc/hexane) to afford 1.6 g of 5.3b as red thick syrup.

Preparation of 5.4b: 5.3b (1.0 g, 3.27 mmol) in DCM (20 mL) was mixed with DMP (1.5 eq) at 0° C., then at RT for 16 hr. The reaction mixture was filtered through a celite bed.

The filtrate was concentrated and the material was purified by column chromatography (20% EtOAc/hexane) to afford 300 mg of 5.4b.

Preparation of Compound 5: 5.4b (300 mg, 0.98 mmol) in MeOH (10 mL) was reacted with valiolamine (0.8 eq), catalytic AcOH, and $NaCNBH_3$ (1.5 eq) at RT for 16 hr. Volatiles were removed and preparative HPLC purification afforded 100 mg of Compound 5 as orange solid. Proton NMR (500 MHz, $CD_3OD$): δ 8.79 (s, 1H), 8.32-8.21 (m, 1H), 7.91 (s, 2H), 7.21 (dd, 1H), 3.75 (t, 1H), 3.59-3.51 (m, 2H), 3.39-3.35 (m, 2H), 3.34-3.31 (m, 2H), 3.10-3.05 (m, 1H), 2.85-2.80 (m, 1H), 2.59-2.51 (m 1H), 2.01 (dd, 1H), 1.82-1.75 (m, 2H), 1.61-1.42 (m, 7H). Calculated Mass: 480.5. Observed Mass: 481.4 (M+H).

Example 6: Synthesis of (1S,2S,3R,4S,5S)-1-(hydroxymethyl)-5-((6-((2-nitro-4-(1H-1,2,3-triazol-1-yl)phenyl)amino)hexyl)amino)cyclohexane-1,2,3,4-tetraol (Compound 6)

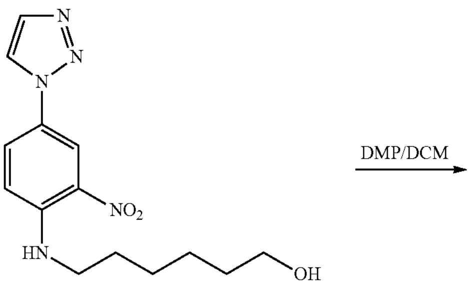

5.3a

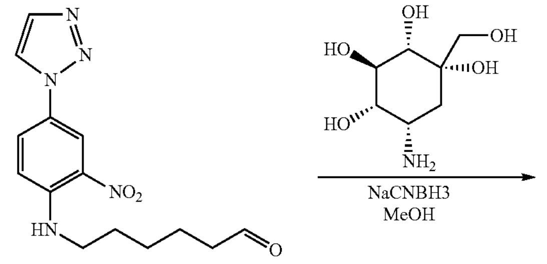

6.1

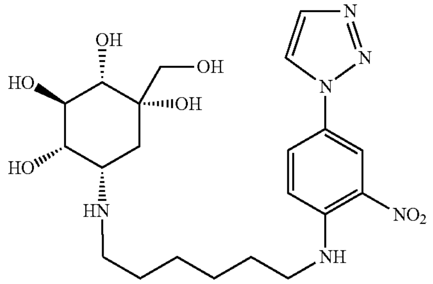

6

Preparation of 6.1: 5.3a (300 mg, 0.98 mmol, from Example 5) in DCM (20 mL) was mixed with DMP (1.5 eq.) at 0° C., then raised to RT for 16 hr. The reaction was filtered through a celite bed. The filtrate was concentrated and the material was purified by column chromatography (40% EtOAc/hexane) to afford 200 mg of 6.1.

Preparation of Compound 6: 6.1 (200 mg, 0.65 mmol) in MeOH (10 mL) was reacted with valiolamine (0.8 eq), catalytic AcOH, and $NaCNBH_3$ (1.5 eq) at RT for 16 hr.

Volatiles were removed and preparative HPLC purification afforded 70 mg of Compound 6 as orange solid. Proton NMR (400 MHz, $CD_3OD$): δ 8.57 (d, J=2.7 Hz, 1H), 8.49 (d, J=1.0 Hz, 1H), 7.99 (dd, J=9.3, 2.7 Hz, 1H), 7.88 (d, J=1.1 Hz, 1H), 7.24 (d, J=9.4 Hz, 1H), 3.72 (t, J=9.8 Hz, 1H), 3.57-3.43 (m, 4H), 3.40-3.32 (m, 1.93H), 3.12-3.04 (m, 1H), 2.85-2.75 (m, 1.13H), 2.53-2.45 (m, 1.03H), 2.00 (dd, J=14.9, 3.2 Hz, 1.02H), 1.82-1.73 (m, 1.99H), 1.60-1.42 (m, 7.12H). Calculated Mass: 480.5. Observed Mass: 481.1 (M+H).

Example 7: Synthesis of (1S,2S,3R,4S,5S)-1-(hydroxymethyl)-5-((6-((2-nitro-4-(pyrimidin-2-yl)phenyl)amino)hexyl)amino)cyclohexane-1,2,3,4-tetraol (Compound 7)

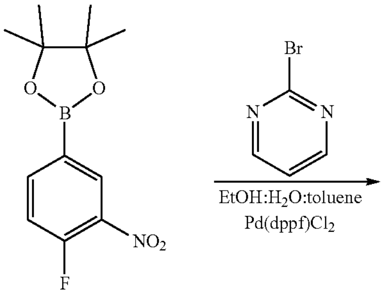

7.1

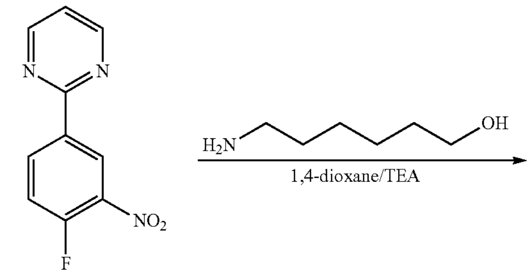

7.2

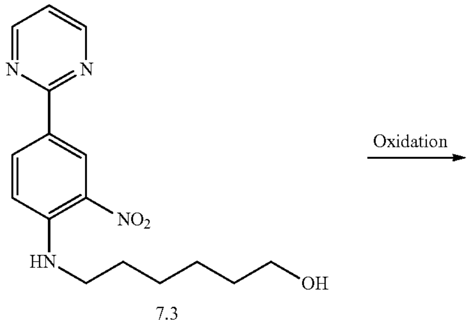

7.3

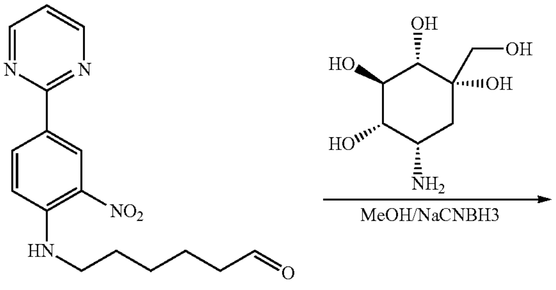

7.4

-continued

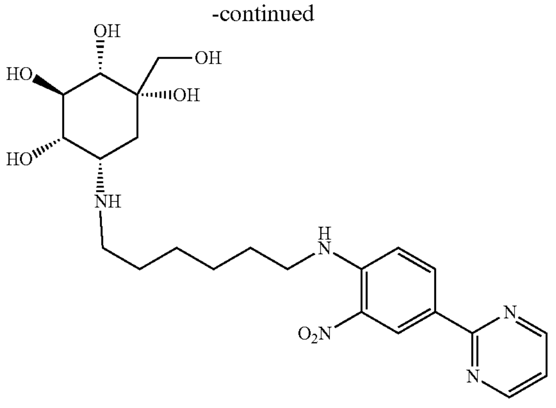

7

Preparation of 7.4 was carried out as described in WO 2016073652 A1. In brief, 7.1 in EtOH/toluene/water (1:1:1) was coupled to 2-bromopyrimidine (1.2 eq) in the presence of $Na_2CO_3$ (3.0 eq) and $Pd(dppf)_2Cl_2$. The reaction was quenched with water and extracted with EtOAc (2×30 mL). The combined organic layer was washed with water, dried over $Na_2SO_4$, filtered, concentrated and purified by silica chromatography (30% EtOAc/hexane) to afford 7.2. 7.2 was coupled to aminohexanol in 1,4-dioxane and TEA. The reaction was quenched with water and extracted with EtOAc (2×30 mL). The combined organic layer was washed with water, dried over $Na_2SO_4$, filtered, concentrated and purified by silica chromatography (50% EtOAc/hexane) to afford 7.3. 7.3 (250 mg, 0.70 mmol) in THF (5 mL) was reacted with $(COCl)_2$ (2.1 eq) and DMSO (2.6 eq) at −78° C. for 2 hr. The reaction mixture was quenched with TEA (5.4 eq) and ice cold water (20 mL), and extracted with DCM (2×30 mL). The combined organic layers were dried over $Na_2SO_4$, filtered and concentrated to afford 200 mg of 7.4 as colorless thick syrup.

Preparation of Compound 7: 7.4 (200 mg) in MeOH (5 mL) was reacted with valiolamine (0.8 eq), catalytic AcOH and $NaCNBH_3$ (1.5 eq) at RT for 16 h. The reaction was concentrated, then purified by preparative HPLC to give 200 mg of Compound 7 with 96% HPLC purity as an orange solid. Proton NMR (400 MHz, $CD_3OD$): δ 9.23 (d, J=2.1 Hz, 1H), 8.78 (d, J=4.9 Hz, 2H), 8.52 (dd, J=9.2, 2.1 Hz, 1H), 7.28 (t, J=4.8 Hz, 1H), 7.14 (d, J=9.2 Hz, 1H), 3.75-3.69 (m, 1H), 3.56-3.50 (m, 2H), 3.49-3.43 (m, 2H), 3.39-3.35 (m, 1H), 3.14-3.08 (m, 1H), 2.92-2.71 (m, 1H), 2.60-2.43 (m, 1H), 2.02 (dd, J=15.0, 3.2 Hz, 1H), 1.82-1.73 (m, 2H), 1.65-1.38 (m, 7H). Calculated Mass: 491.5. Observed Mass: 492.3 (M+H).

Example 8: Synthesis of (1S,2S,3R,4S,5S)-5-((4-((4-azido-2-nitrophenyl)amino)butyl)amino)-1-(hydroxymethyl)cyclohexane-1,2,3,4-tetraol (Compound 8)

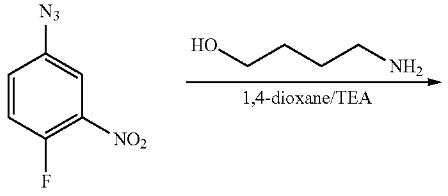

8.1

-continued

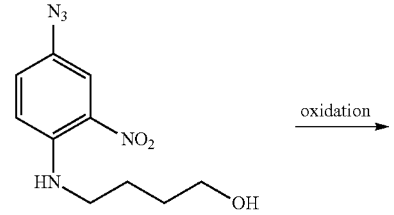

8.2

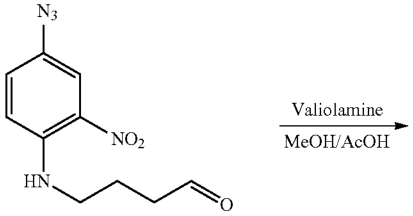

8.3

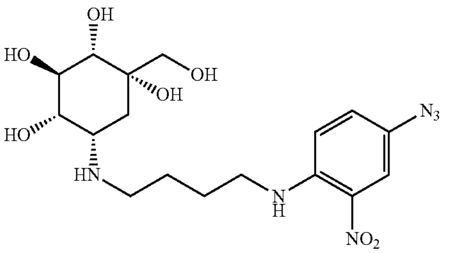

8

Preparation of 8.2: 8.1 (4-fluoro-3-nitrophenyl azide or 1-fluoro-2-nitro-4-azidobenzene or FNAB) (500 mg, 2.74 mmol) in 1,4-dioxane (10 mL) was reacted with aminobutanol (2.0 eq) and TEA (3 eq) at 80° C. for 16 hr. Reaction was cooled to RT and quenched with ice-cold water. The aqueous layer was extracted with EtOAc (2×20 mL). Combined organic layer was dried over $Na_2SO_4$, filtered and concentrated. The material was purified by silica chromatography (50% EtOAc/hexane) to afford 600 mg of 8.2 as orange red solid.

Preparation of 8.3: 8.2 (500 mg, 1.99 mmol) in DCM (10 mL) was mixed with DMP (1.5 eq) at 0° C., raised to RT, and reacted for 2 hr. The reaction was quenched with saturated $NaHCO_3$ solution (10 mL) and extracted with DCM (2×10 mL). The combined organic layer was dried over $Na_2SO_4$, filtered, concentrated, and purified on silica (30% EtOAc/Hexane) to give 140 mg of 8.3 as orange red solid.

Preparation of Compound 8: 8.3 (140 mg, 0.56 mmol) in MeOH (5 mL) was reacted with valiolamine (0.8 eq), catalytic AcOH and $NaCNBH_3$ (1.5 eq) at RT for 16 hr. The volatiles were concentrated and purified by preparative HPLC to afford 72 mg of Compound 8 as orange red thick syrup. Proton NMR (400 MHz, $CD_3OD$): δ 7.81 (d, J=2.8 Hz, 1H), 7.28 (dd, J=9.3, 2.8 Hz, 1H), 7.12 (d, J=9.3 Hz, 1H), 3.78-3.69 (m, 1H), 3.66-3.59 (m, 1H), 3.56 (d, J=10.9 Hz, 1H), 3.49-3.42 (m, 2H), 3.42-3.37 (m, 2H), 3.21-2.99 (m, 2H), 2.95-2.76 (m, 1H), 2.15-2.09 (m, 1H), 1.86-1.72 (m, 4H), 1.71-1.62 (m, 1H). Calculated Mass: 426.4. Observed Mass: 427.1 (M+H), 449.2 (M+Na).

Example 9: Synthesis of (1S,2S,3R,4S,5S)-5-((5-((4-azido-2-nitrophenyl)amino)pentyl)amino)-1-(hydroxymethyl)cyclohexane-1,2,3,4-tetraol (Compound 9)

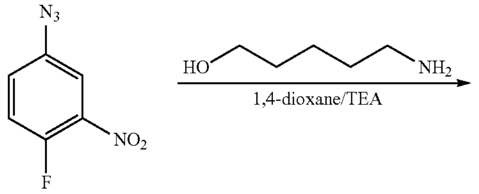

9.1

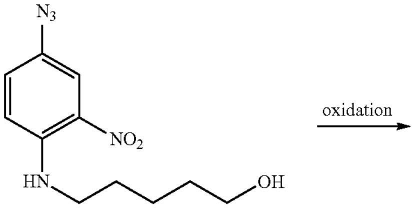

9.2

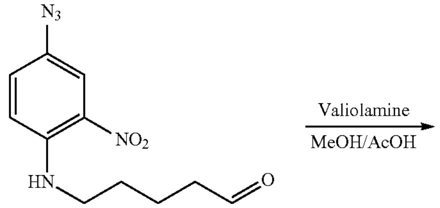

9.3

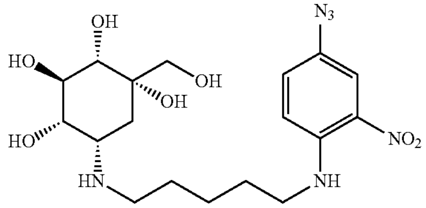

9

Preparation of 9.2: 9.1 (FNAB) (1 g, 2.28 mmol) in 1,4-dioxane (20 mL) was mixed with aminopentanol (1.5 eq) and TEA (3 eq) at RT, and raised to 80° C. for 16 hr. The mixture was cooled to RT and the volatiles were removed. The residue was dissolved in water and extracted with EtOAc (2×30 mL). The organic layer was dried over $Na_2SO_4$, filtered, concentrated, and purified by silica gel column chromatography (20% EtOAc/Hexane) to afford 1.2 g of 9.2 as orange red thick syrup.

Preparation of 9.3: 9.2 (250 mg, 0.94 mmol) in THF (5 mL) was reacted with $(COCl)_2$ (2.1 eq) and DMSO (2.6 eq) at −78° C. for 2 hr. The reaction was quenched with TEA (5.4 eq) and ice cold water (20 mL), then extracted with DCM (2×30 mL). The combined organic layer was dried over $Na_2SO_4$, filtered, and concentrated under reduced pressure to afford 180 mg of 9.3 as colorless thick syrup.

Preparation of Compound 9: 9.3 (180 mg) in MeOH (5 mL) was reacted with valiolamine (0.8 eq), catalytic AcOH and $NaCNBH_3$ (1.5 eq) at RT for 16 hr. The reaction was concentrated to afford 250 mg of material and purified by preparative HPLC to afford 28 mg of Compound 9 as orange red thick syrup with 96% HPLC purity. Proton NMR (400 MHz, $CD_3OD$): δ 8.11 (br, 1H), 7.81 (d, J=2.8 Hz, 1H), 7.28 (dd, J=9.3, 2.8 Hz, 1H), 7.11 (d, J=9.3 Hz, 1H), 3.81-3.67 (m, 1H), 3.62-3.51 (m, 2H), 3.45-3.34 (m, 4H), 3.27-3.17 (m, 1H), 3.00-2.87 (m, 1H), 2.74-2.59 (m, 1H), 2.11-2.03 (m, 1H), 1.82-1.71 (m, 2H), 1.70-1.46 (m, 5H). Calculated Mass: 440.4. Observed Mass: 441.3 (M+H).

Example 10: Synthesis of (1S,2S,3R,4S,5S)-5-((2-(2-((4-azido-2-nitrophenyl)amino)ethoxy)ethyl)amino)-1-(hydroxymethyl)cyclohexane-1,2,3,4-tetraol (Compound 10)

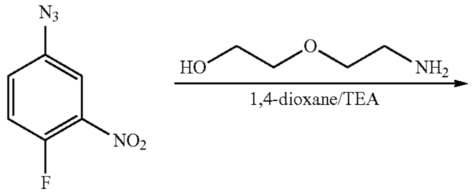

10.1

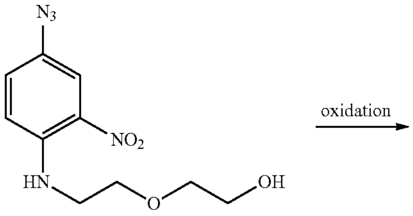

10.2

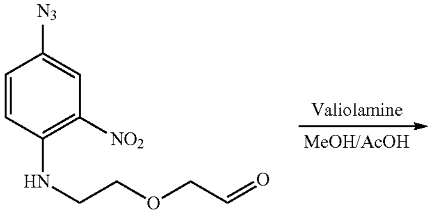

10.3

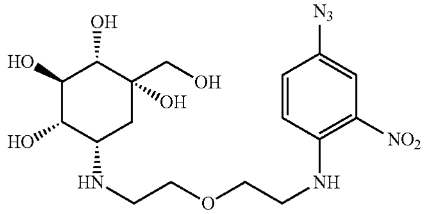

10

Preparation of 10.2: 10.1 (FNAB) (500 mg, 2.74 mmol) in 1,4-dioxane (10 mL) was reacted with 2-(2-aminoethoxy)ethan-1-ol (2.0 eq) and TEA (3 eq) at 80° C. for 16 hr. The reaction was cooled to RT and quenched with ice-cold water. The aqueous layer was extracted with EtOAc (2×20 mL). The organic layer was dried over $Na_2SO_4$, filtered, concentrated, and purified by silica chromatography (50% EtOAc/hexane) to afford 700 mg of 10.2 as orange red solid.

Preparation of 10.3: 10.2 (200 mg, 0.74 mmol) in DCM (50 mL) was reacted with oxalyl chloride (2.1 eq) and DMSO (2.6 eq) at −78° C. for 2 hr. The reaction was quenched with TEA (5.4 eq), then ice cold water (10 mL), and extracted with DCM (2×10 mL). The combined organic layer was dried over $Na_2SO_4$, filtered and concentrated under reduced pressure. The material was purified by silica gel (30% EtOAc/Hexane) to afford 150 mg of 10.3 as orange red solid.

Preparation of Compound 10: 10.3 (150 mg, 0.56 mmol) in MeOH (7 mL) was reacted with valiolamine (0.8 eq), catalytic AcOH and $NaCNBH_3$ (1.5 eq) at RT for 16 hr. The volatiles were concentrated under reduced pressure and purified by preparative HPLC to afford 90 mg of Compound 10 as an orange red solid. Proton NMR (400 MHz, $CD_3OD$): δ 8.24 (br s, 1H), 7.80 (d, J=2.6 Hz, 1H), 7.27 (dd, J=9.3, 2.8 Hz, 1H), 7.14 (d, J=9.3 Hz, 1H), 3.80-3.71 (m, 3H), 3.70-3.63 (m, 1H), 3.63-3.49 (m, 5H), 3.38-3.36 (m, 1H), 3.34 (d, J=4.3 Hz, 1H), 3.13-3.08 (m, 1H), 2.98-2.90 (m, 1H), 2.75-2.67 (m, 1H), 2.01 (dd, J=15.1, 3.3 Hz, 1H), 1.47 (dd, J=2.7, 15.0 Hz, 1H). Calculated Mass: 442.4. Observed Mass: 443.2 (M+H), 465.1 (M+Na).

Example 11: Synthesis of 5-(((1S,2S,3R,4S,5S)-2,3,4,5-tetrahydroxy-5-(hydroxymethyl)cyclohexyl)amino)pentanoic acid (Compound 11)

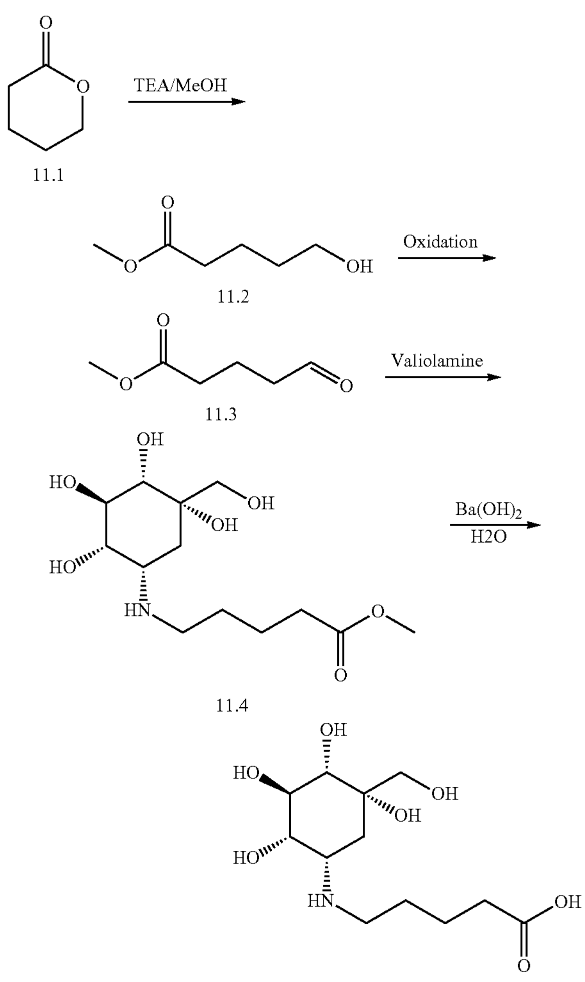

11.1

11.2

11.3

11.4

11

Preparation of 11.2: 11.1 (5 g, 50.0 mmol) in MeOH (50 mL) was reacted with TEA (0.1 eq) at RT for 16 hr. The volatiles were concentrated under reduced pressure. The material was purified by silica gel column chromatography (30% EtOAc/Hexane) to afford 4 g of 11.2 as colorless liquid.

Preparation of 11.3: 11.2 (4 g, 3.37 mmol) in DCM (30 mL) was reacted with $(COCl)_2$ (2.1 eq) and DMSO (2.6 eq) at −78° C. for 2 hr. The reaction was quenched with TEA (5.4 eq) and ice cold water (20 mL), and extracted with DCM (2×40 mL). The combined organic layer was dried over $Na_2SO_4$, filtered, and concentrated to afford 1.6 g of 11.3 as colorless thick syrup.

Preparation of 11.4: 11.3 (1.6 g, 12.3 mmol) in MeOH (30 mL) was reacted with valiolamine (0.8 eq), catalytic AcOH, and $NaCNBH_3$ (1.5 eq) at RT for 16 hr. The volatiles were concentrated and purified by silica gel column chromatography (20% MeOH/DCM, 10% $NH_4OH$) to afford 800 mg of 11.4 as colorless thick syrup.

Preparation of Compound 11: 11.4 (800 mg, 2.76 mmol) in 15 mL $H_2O$ was mixed with $Ba(OH)_2$ (2.0 eq) at RT, and increased to 80° C. for 6 hr. The reaction was quenched with dry ice (pH=7) and the obtained solid was filtered through a celite bed and washed with water (10 mL). The filtrate was concentrated and triturated with EtOAc (2×30 mL) then Me0H (2×20 mL) followed by lyophilization (3 days) to afford 220 mg of Compound 11 as off-white solid. Proton NMR (400 MHz, $D_2O$): δ3.93-3.77 (m, 2H), 3.68-3.53 (m, 4H), 3.35-3.24 (m, 1H), 3.15-3.04 (m, 1H), 2.35-2.23 (m, 3H), 1.84 (dd, J=16.1, 3.7 Hz, 1H), 1.79-1.57 (m, 4H). Calculated Mass: 293.3. Observed Mass: 294.2 (M+H).

Example 12: Synthesis of 2-((4-azido-2-nitrophenyl)amino)ethyl (2-(((1S,2S,3R,4S,5S)-2,3,4,5-tetrahydroxy-5-(hydroxymethyl)cyclohexyl)amino)ethyl) carbamate (Compound 12)

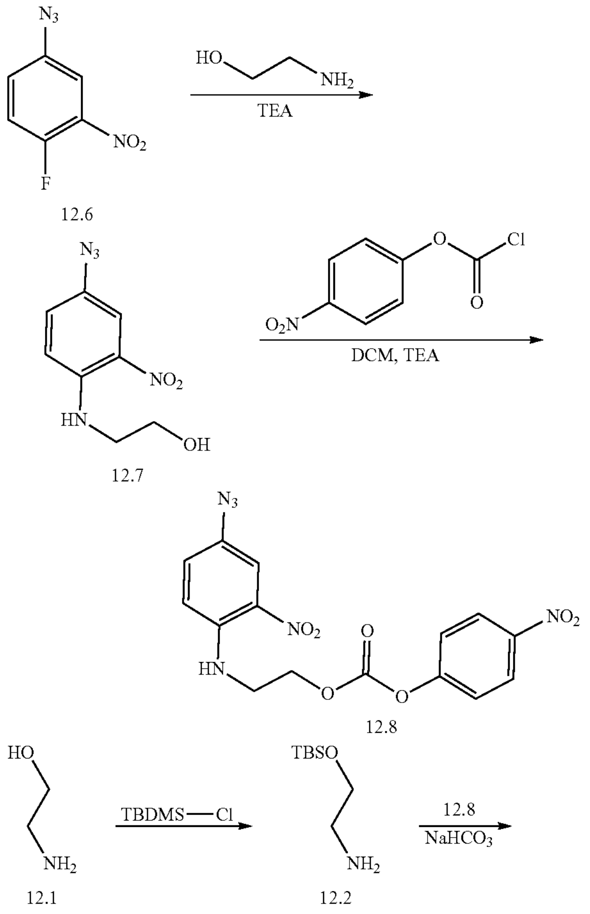

12.6

12.7

12.8

12.1

12.2

-continued

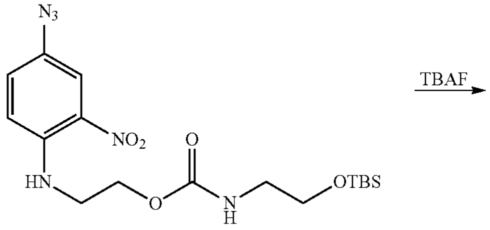

12.3

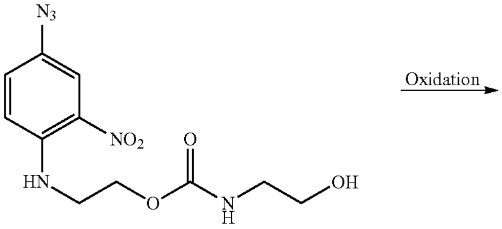

12.4

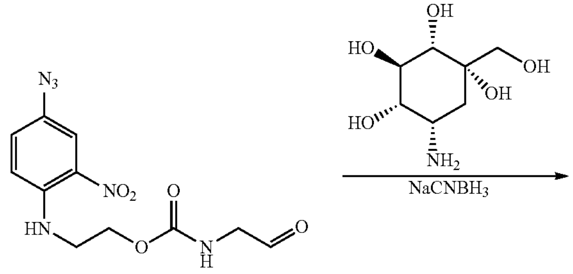

12.5

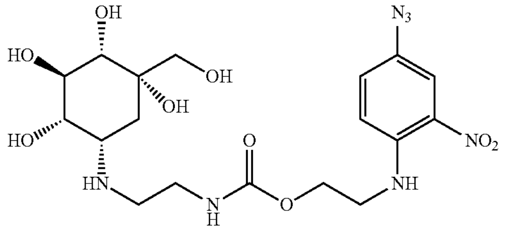

12

Preparation of 12.2: 12.1 (2-aminoethanol) (5 g, 81.96 mmol) in DCM (120 mL) was reacted with imidazole (2 eq) and TBS-Cl (0.9 eq) at RT for 2 hr. The reaction was diluted with water (400 mL) then extracted with DCM (200 mL×2). Combined organic layer was dried over $Na_2SO_4$, filtered and concentrated to afford 8 g of 12.2.

Preparation of 12.7: 12.6 (FNAB) (3 g, 16.4 mmol) in 1,4-dioxane (60 mL) was reacted with TEA (3 eq) and aminoethanol (1.5 eq) at 100° C. for 12 hr. The reaction was cooled to RT and the solvent was removed. The residue was dissolved in water (200 mL) and extracted with EtOAc (200 mL×2). The organic layer was dried over $Na_2SO_4$, filtered and concentrated. The material was purified by silica gel column chromatography (30% EtOAc/hexane) to afford 2 g of 12.7.

Preparation of 12.8: 12.7 (500 mg, 2.24 mmol) in DCM (20 mL) was mixed with TEA (2 eq) and 4-nitrophenyl chloroformate (1.5 eq) at 0° C., and raised to RT for 12 hr. The reaction mixture was quenched with water (20 mL) and extracted with DCM (15 mL×2). The organic layer was dried over $Na_2SO_4$, filtered and concentrated. The material was crystallized from methanol to afford 600 mg of 12.8.

Preparation of 12.3: 12.8 (600 mg, 1.546 mmol) in THF (20 mL) was reacted with 12.2 (1 eq) and $NaHCO_3$ (4 eq) at 100° C. in a sealed tube for 12 hr. The reaction mixture was filtered and concentrated. The material was purified by silica gel column chromatography (3% EtOAc/hexane) to afford 400 mg of 12.3.

Preparation of 12.4: 12.3 (400 mg, 0.943 mmol) in THF (10 mL) was reacted with 1.0 M TBAF in THF (1.5 eq) at 0° C. for 2 hr. The reaction was quenched with water (20 mL) and extracted with EtOAc (10 mL×2). The organic layer was dried over $Na_2SO_4$, filtered and concentrated. The material was purified by silica gel column chromatography (40% EtOAc/hexane) to afford 150 mg of 12.4.

Preparation of 12.5: 12.4 (150 mg, 0.483 mmol) in DCM was reacted with $(COCl)_2$ (2 eq) and DMSO (4 eq) at −78° C. for 4 h. The reaction was quenched with TEA (6 eq) then water (20 mL), and extracted with DCM (10 mL×2). The organic layer was dried over $Na_2SO_4$, filtered and concentrated to afford 150 mg of 12.5 used in the next step without further purification.

Preparation of Compound 12: 12.5 (150 mg) in MeOH was reacted with valiolamine (1 eq) and $NaCNBH_3$ (1.5 eq) at RT for 12 hr. Solvent was removed and preparative HPLC purification afforded 40 mg of Compound 12 with 99% HPLC purity. Proton NMR (400 MHz, $CD_3OD$): δ 7.81 (d, J=2.6 Hz, 1H), 7.28 (dd, J=9.2, 2.7 Hz, 1H), 7.21-7.13 (m, 1H), 4.37-4.24 (m, 2H), 3.76-3.59 (m, 3H), 3.56-3.43 (m, 2H), 3.37-3.33 (m, 2H), 3.28-3.16 (m, 2H), 3.09-3.06 (m, 1H), 2.90-2.82 (m, 1H), 2.62-2.54 (m, 1H), 2.09-1.86 (m, 1H), 1.57-1.37 (m, 1H). Calculated Mass: 485.4. Observed Mass: 486.4 (M+H).

Example 13: Glucosidase Assays

Preparation of Human Full-length Glucosidase I: The amino acid sequence for human full-length glucosidase I was obtained from UniProt (Q13724). Constructs were cloned into Gateway entry vector, consisting of the full-length open reading frame (ORF) preceded by a Kozac sequence with a 6-His affinity tag added to the C-terminus (SEQ ID NO 1). The entry vector was cloned into Kemp Protein's BacMam Destination vector and transformed into chemically competent DH10Bac *E. coli* cells to produce recombinant glucosidase I bacmids. Bacmid isolates were obtained following two rounds of blue-white screening and they were transfected into Sf9 cells cultivated in serum-free medium (Thermo Fisher Scientific). After four days post-transfection, the culture supernatants containing virus were harvested and filter sterilized. The virus titer was determined using a plaque assay on Sf9 cell monolayers and expressions were performed using HEK-293T cells cultivated in serum-free Feestyle-293 medium (Thermo Fisher). A multiplicity of infection (MOI, ratio of virus to cells) of 4 was selected. Soluble glucosidase I was detected by anti-His western blots in the soluble cell extract following extraction with 1% V/V NP40 for 30 minutes at 0° C. Productions and purifications of glucosidase I were carried out at scales ranging from 1-liter to 10-liters. In one example, production at the 1-liter scale was performed in shake-flasks at 27° C. and 100 rpm using HEK-293T cells cultivated in Freestyle-293 medium under serum-free conditions. In another example, production at the 10-liter scale was performed in stirred-tank bioreactors at 27° C. and 80 rpm with dissolved oxygen level at 50% of oxygen in air and pH between 7.0 and 7.2. Cells were transduced at MOI of 4 and the cell pellet was harvested at 48 hours post-transduction using centrifugation.

The pellet from a 10-liter culture was lysed by resuspending the pellet into 1-liter of 50 mM $NaH_2PO_4—H_2O$, 300 mM NaCl, 10 mM Imidazole, 1 mM PMSF, and 1% V/V NP40 at pH 8. The suspension was incubated on ice for 30 minutes and clarified at 500 g and 4° C. The supernatant was collected and clarified at 20,000 g for 30 minutes at 4° C. and the supernatant was collected and filtered through a 0.2 micron filter. The lysate was loaded onto a 25 mL Ni-NTA Superflow (Qiagen) column (26×60 mm) at a flow rate of 10 mL per minute. The column was washed with 20 column volumes (CV) of 50 mM $NaH_2PO_4$—$H_2O$, 300 mM NaCl and 10 mM Imidazole at pH 8 and eluted using a linear gradient of 0-60% of 50 mM $NaH_2PO_4$—$H_2O$, 300 mM NaCl and 500 mM Imidazole at pH 8 over 90 minutes at 5 mL per minute. Fractions (25 mL) were collected and analyzed by SDS PAGE and Western Blot (reducing anti-His). Fractions containing purified glucosidase I were pooled and dialyzed into storage buffer (20 mM Tris, 300 mM NaCl, 50 mM L-arginine, 10 mM EDTA and 0.01% V/V Tween 80 pH 7.5). The final material was filter sterilized and stored at 4° C., and the working dilution was confirmed by a use-test in the indicated assay conditions prior to use.

Alpha-glucosidase I Assay: The assay was performed by incubating recombinant alpha-glucosidase I enzyme with multiple dilutions of test compounds for 60 minutes at 37° C. A synthetic trisaccharide substrate analog disclosed by Scaman, C. H., et al., *Carbohydrate Research,* 296, 203-213 (1996), the entirety of which is hereby incorporated by reference, was then introduced to the mixture for 90 minutes at 37° C. The reaction was then stopped with 1.5 M Tris (pH 8). In the absence of inhibition, the terminal glucose of the substrate was hydrolyzed by the enzyme. The D-glucose product was detected using Amplex Red Glucose/Glucose Oxidase Assay Kit (Invitrogen) following the manufacturer's directions where glucose oxidase reacts with D-glucose to form D-gluconolactone and $H_2O_2$ which then reacts with the Amplex Red reagent to generate a red-fluorescent oxidation product (560 nm, excitation; 590 nm, emission). Compounds inhibiting glucosidase I inhibit the cleavage of the substrate and result in lower signals. Percent inhibition is plotted as a function of concentration for each compound, compared to control reactions. The $IC_{50}$ was determined using a 4-PL curve fit and serves as a measure of relative inhibitory activity of each test compound (see Table 4).

Preparation of Murine Full-length Glucosidase II: Glucosidase is a heterodimeric protein consisting of alpha and beta subunits. The amino acid sequence for the alpha (SEQ ID NO: 2) and beta (SEQ ID NO: 3) subunits are full-length murine glucosidase II. A single construct was designed for each of the subunits for gene synthesis and cloning into Gateway entry vectors. The alpha subunit was appended with a Strep-affinity tag and the beta subunit was appended with a 6-His affinity tag. The entry vectors were cloned into Kemp Protein's BacMam Destination vector and the vectors were transformed into chemically competent DH10Bac *E. coli* cells to produce recombinant glucosidase II bacmids. Bacmid isolates for each of the subunits were obtained following two rounds of blue-white screening and they were transfected into Sf9 cells cultivated in serum-free medium (Thermo Fisher Scientific). MOI of 10 with a ratio of 75% alpha subunit and 25% beta subunit was selected for expression of glucosidase II. Glucosidase II was detected in the culture supernatant and the proteins were detected using Western Blots probed with anti-His and anti-Strep antibodies. Productions and purifications of glucosidase II were carried out at scales ranging from 1-liter to 10-liters. In one example, production at the 1-liter scale was performed in shake-flasks at 27° C. and 100 rpm using HEK-293T cells cultivated in Freestyle-293 medium under serum-free conditions. In another example, production at the 10-liter scale was performed in stirred-tank bioreactors at 27° C. and 80 rpm with dissolved oxygen level maintained at 50% of oxygen in air and pH maintained between 7.0 and 7.2. For both subunits, the cells were transduced using a total MOI of 10 (75% alpha and 25% beta) and the culture supernatant was harvested at 96 hours post-transduction using centrifugation and filtration through a 0.2 micron filter.

The supernatant from a 10-liter culture was placed in a stir-jar and 25 mL of Nickel-SEPHAROSE Excel resin (GE) was added. The supernatant was stirred overnight at 25 rpm and 4° C. and the resin was collected into a column (26 mm×60 mm) and washed with 8 CV of 2×DPBS at pH 7.4. The glucosidase II protein was eluted using a linear gradient of 0-60% of 2×DPBS and 500 mM imidazole at pH 7.4. Fractions (10 mL) were collected and analyzed by SDS PAGE and Western Blot (reducing anti-His and anti-Strep). Fractions containing purified glucosidase II were pooled and concentrated for application to a SUPERDEX 200 (26 mm×600 mm) column (GE). The column buffer was PBS pH 7.2 and the concentrated eluate pool was loaded at a rate of 1 mL per minute. Fractions (3 mL) were collected and analyzed using SDS PAGE and Western Blot (reducing anti-His and anti-Strep). Fractions containing purified glucosidase II in PBS pH 7.2 were pooled and concentrated to 1 mg/mL. The final product was filter sterilized and stored at 4° C.

Alpha-glucosidase II Assay: The assay was performed by incubating recombinant enzyme alpha-glucosidase II for 60 minutes at 37° C. with multiple dilutions of test compounds. 4-methylumbelliferyl-alpha-D-pyranoside was then introduced as the substrate to the mixture. Fluorogenic 1,4-methyllumbelliferone was generated, and the reaction was stopped with the stop solution (0.5 M glycine, 0.3 M NaOH pH 10) after an incubation of 30 minutes at 37° C. 1,4-methyllumbelliferone was detected by fluorescence (excitation at 365 nm, emission at 440 nm). Percent inhibition was then plotted as a function of concentration for each test compound. The 50% inhibitory concentration ($IC_{50}$) is determined using a 4-PL curve fit and serves as a measure of relative inhibitory activity of each test compound (see Table 4).

Acid alpha-glucosidase (GAA): To analyze inhibitory effects of a test compound, commercially available recombinant human GAA was incubated with multiple dilutions of test compound for 60 minutes at 37° C. 4-methylumbelliferyl-alpha-D-pyranoside was then introduced to the mixture as the substrate. 1,4-methyllumbelliferone is generated, and after an incubation for 20 minutes at 37° C., the reaction was stopped with the stop solution (0.5 M glycine 0.3 M NaOH pH 10). 1,4-methyllumbelliferone is detected by fluorescence (excitation at 365 nm, emission at 440 nm). Relative fluorescence is compared to untreated enzymatic activity and test compound concentration is plotted as a function of percent inhibition. The $IC_{50}$ is determined using a 4-PL curve fit as the measure of relative inhibitory activity of each test compound (see Table 4).

Beta-glucocerebrosidase (GBA, also referred to glucosylceramidase): To analyze inhibitory effects of a test compound, commercially available recombinant human GBA was incubated with multiple dilutions of test compound for 60 minutes at 37° C. 4-methylumbelliferyl-beta-D-pyranoside was then introduced to the mixture as substrate. Following incubation for 60 minutes at 37° C., 1,4-methyllumbelliferone was generated, and the reaction was stopped with the stop solution (0.5 M glycine; 0.3 M NaOH, pH 10). 1,4-methyllumbelliferone was detected by fluorescence (excitation at 365 nm, emission at 440 nm). Relative fluorescence is compared to untreated enzymatic activity and test compound concentration is then plotted as a function of percent inhibition. The $IC_{50}$ was determined using a 4-PL curve fit as the measure of relative inhibitory activity of each test compound (see Table 4).

Intestinal alpha-glucosidases (rat maltase and sucrase): Intestinal alpha-glucosidases act upon 1,4-alpha-glucoside bonds, breaking down disaccharides to glucose. To perform this assay, partially purified alpha-glucosidase from intestinal rat powder was incubated for 60 minutes at 37° C. with multiple dilutions of test compounds. Maltose or Sucrose respectively was then introduced as substrate to the mixture and incubated for 30 minutes at 37° C. The reaction was stopped by a 5-minute incubation at 90° C. and the resultant glucose production is detected using Sigma's Glucose GO Kit. Percent inhibition was then plotted as a function of concentration for each test compound. The $IC_{50}$ was determined using a 4-PL curve fit and serves as the measure of relative inhibition of each test compound (see Table 4). Table 4 summarizes the results of IC50s for each molecule against each tested glucosidase enzyme.

TABLE 4

| Compound | GAA | GBA | sucrase | maltase | aGlc1 | aGlc2 |
|---|---|---|---|---|---|---|
| Valiolamine | 14.83 | >1000 | 0.334005 | 1.298572 | 87.3900 | >>100 |
| Compound 1 | 45.38 | >1000 | 0.070006 | 1.468337 | 29.5400 | 38.69 |
| Compound 2 | 0.839 | 138.6 | <0.0333 | 0.001648 | 0.7300 | 0.0337 |
| Compound 3 | 11.63 | >1000 | 0.116101 | 0.101726 | 10.7700 | 0.4902 |
| Compound 4 | 24.8 | >1000 | 2.928823 | 0.512266 | 32.0500 | 1.419 |
| Compound 5 | 0.514 | 142.9 | 0.034241 | <0.0333 | 0.0479 | <<0.001 |
| Compound 6 | 1.196 | 776.3 | 0.06736 | <0.0333 | 1.2700 | 0.0155 |
| Compound 7 | 0.377 | >1000 | N/A | 0.008144 | 0.6439 | 0.0011 |
| Compound 8 | 0.707 | >1000 | N/A | 0.0053 | 2.4220 | 1.01 |
| Compound 9 | 0.9888 | 102.7 | 0.011174 | 0.004856 | 0.4117 | 0.027 |
| Compound 10 | 8.218 | >1000 | N/A | 0.0261 | 3.6640 | 37.00 |
| Compound 11 | 227.8 | >1000 | 3.163 | 7.576 | 89.8900 | >>100 |
| Compound 12 | N/A | N/A | N/A | N/A | 1.1284 | N/A |

What is claimed is:

1. A compound according to Formula (I):

I

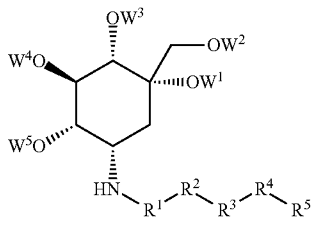

or a pharmaceutically acceptable salt thereof, wherein $W^1$-$W^5$ are each independently selected from the group consisting of —H, benzyl, —C(═O)—$C_1$-$C_9$ alkyl, and —C(═O)O—$C_1$-$C_9$ alkyl;

$R^1$ is optionally substituted $C_1$-$C_9$ alkylene;

$R^2$ is absent or selected from the group consisting of —NH—, —O—, —C(═O)—, and —NH—C(═O)O—;

$R^3$ is absent or selected from the group consisting of —O—, —C(═O)—, —C(═O)O, and optionally substituted $C_1$-$C_6$ alkylene;

$R^4$ is —NH—;

$R^5$ is

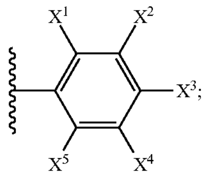

wherein $X^1$, $X^2$, $X^3$, $X^4$, and $X^5$ are each independently selected from the group consisting of —H, —$NO_2$, —$N_3$, optionally substituted $C_2$-$C_{12}$ heterocycle, and optionally substituted $C_1$-$C_{12}$ heteroaryl.

2. The compound of claim 1, wherein $W^1$-$W^5$ are each independently —H.

3. The compound of claim 2, wherein $R^1$ is a $C_1$-$C_9$ alkylene.

4. The compound of claim 1, wherein $R^3$ is a $C_1$-$C_6$ alkylene or —C(═O)O—.

5. The compound of claim 1, wherein $R^5$ is

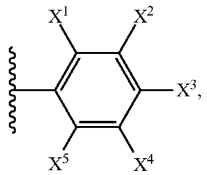

and wherein $X^1$, $X^2$, $X^3$, $X^4$, and $X^5$ are each independently selected from the group consisting of —H, —$NO_2$, —$N_3$, a $C_2$-$C_{12}$ heterocycle, and a $C_1$-$C_{12}$ heteroaryl.

6. The compound of claim 5, wherein $X^3$ is —$N_3$ or a $C_1$-$C_{12}$ heteroaryl.

7. The compound of claim 5, wherein $X^3$ is —$N_3$.

8. The compound of claim 5, wherein $X^3$ is a $C_1$-$C_{12}$ heteroaryl, and wherein the $C_1$-$C_{12}$ heteroaryl is selected from the group consisting of

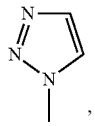 , 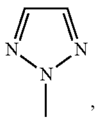 , 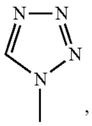 , and 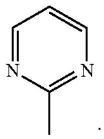 .

9. The compound of claim 5, wherein $X^1$ is —$NO_2$.

10. The compound of claim 5, wherein $X^2$, $X^4$, and $X^5$ are each —H.

11. The compound of claim 1, wherein the compound is selected from the group consisting of:

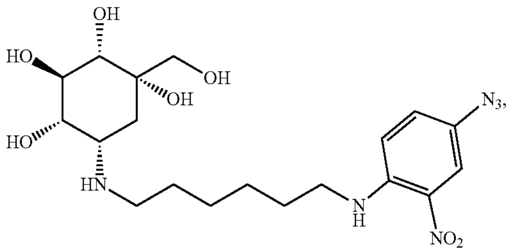

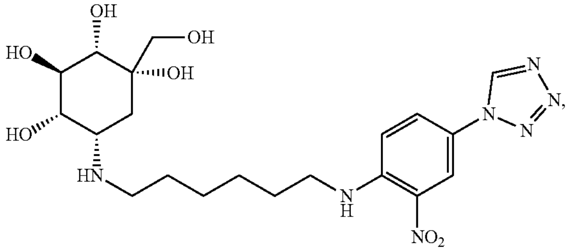

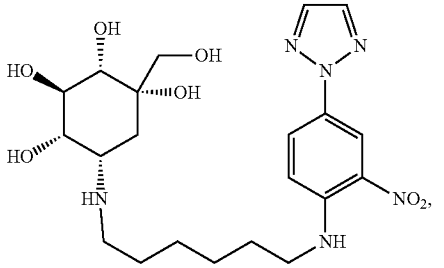

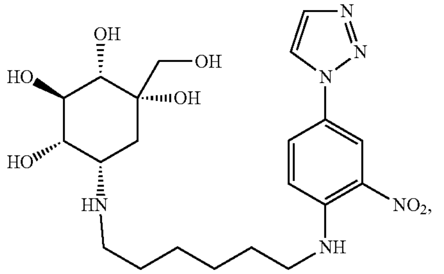

-continued

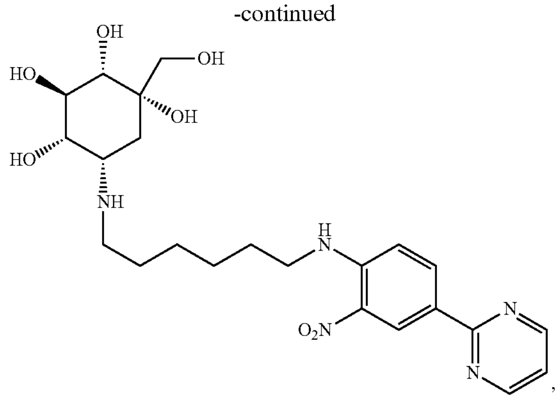

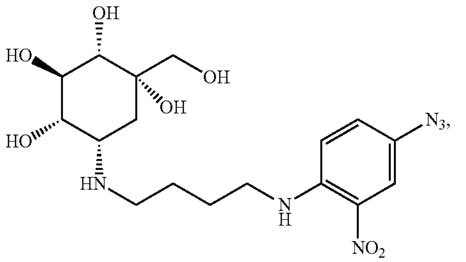

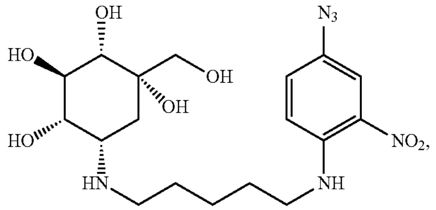

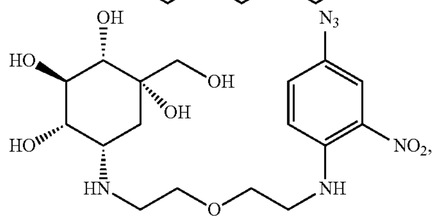

and

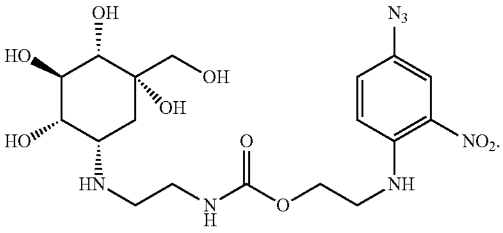

12. A pharmaceutical composition comprising the compound of claim 1 and at least one pharmaceutically acceptable excipient.

13. A method of treating diabetes, the method comprising administering to a subject in need thereof, a therapeutically effective amount of the compound of claim 1.

14. The method of claim 13, wherein the diabetes is Type I diabetes or Type II diabetes.

15. A method for inhibiting glycosidase function, the method comprising administering to a subject in need thereof a therapeutically effective amount of the compound of claim 1.

16. A method for treating or preventing a viral infection, the method comprising administering to a subject in need thereof a therapeutically effective amount of the compound of claim 1.

17. The method of claim 16, wherein the viral infection is selected from the group consisting of hepatitis C virus (HCV) infection, hepatitis B virus (HBV) infection, dengue virus (DENV) infection, Marburg virus (MARV) infection, Ebola virus (EBOV) infection, BVHV, human immunodeficiency virus (HIV) infection, influenza A infection, influenza B infection, encephalitis virus infection, Zika virus infection, and yellow fever virus (YFV) infection.

18. The method of claim 17, wherein the encephalitis virus infection is eastern equine encephalitis virus infection, western equine encephalitis virus infection, and Japanese encephalitis virus (JEV) infection.

19. The compound of claim 1, wherein $R^2$ is —O— or —NH—C(═O)O—.

* * * * *

SEQUENCE LISTING

```
<160> NUMBER OF SEQ ID NOS: 3

<210> SEQ ID NO 1
<211> LENGTH: 843
<212> TYPE: PRT
<213> ORGANISM: Artificial Sequence
<220> FEATURE:
<223> OTHER INFORMATION: Human Full-length Glucosidase I with 6-His
      affinity tag added to the C-terminus

<400> SEQUENCE: 1

Met Ala Arg Gly Glu Arg Arg Arg Arg Ala Val Pro Ala Glu Gly Val
1               5                   10                  15

Arg Thr Ala Glu Arg Ala Ala Arg Gly Gly Pro Gly Arg Arg Asp Gly
            20                  25                  30

Arg Gly Gly Gly Pro Arg Ser Thr Ala Gly Gly Val Ala Leu Ala Val
        35                  40                  45

Val Val Leu Ser Leu Ala Leu Gly Met Ser Gly Arg Trp Val Leu Ala
    50                  55                  60

Trp Tyr Arg Ala Arg Arg Ala Val Thr Leu His Ser Ala Pro Pro Val
65                  70                  75                  80

Leu Pro Ala Asp Ser Ser Ser Pro Ala Val Ala Pro Asp Leu Phe Trp
                85                  90                  95

Gly Thr Tyr Arg Pro His Val Tyr Phe Gly Met Lys Thr Arg Ser Pro
            100                 105                 110

Lys Pro Leu Leu Thr Gly Leu Met Trp Ala Gln Gln Gly Thr Thr Pro
        115                 120                 125

Gly Thr Pro Lys Leu Arg His Thr Cys Glu Gln Gly Asp Gly Val Gly
    130                 135                 140

Pro Tyr Gly Trp Glu Phe His Asp Gly Leu Ser Phe Gly Arg Gln His
145                 150                 155                 160

Ile Gln Asp Gly Ala Leu Arg Leu Thr Thr Glu Phe Val Lys Arg Pro
```

-continued

```
                165                 170                 175

Gly Gly Gln His Gly Gly Asp Trp Ser Trp Arg Val Thr Val Glu Pro
            180                 185                 190

Gln Asp Ser Gly Thr Ser Ala Leu Pro Leu Val Ser Leu Phe Phe Tyr
        195                 200                 205

Val Val Thr Asp Gly Lys Glu Val Leu Leu Pro Glu Val Gly Ala Lys
    210                 215                 220

Gly Gln Leu Lys Phe Ile Ser Gly His Thr Ser Glu Leu Gly Asp Phe
225                 230                 235                 240

Arg Phe Thr Leu Leu Pro Pro Thr Ser Pro Gly Asp Thr Ala Pro Lys
                245                 250                 255

Tyr Gly Ser Tyr Asn Val Phe Trp Thr Ser Asn Pro Gly Leu Pro Leu
            260                 265                 270

Leu Thr Glu Met Val Lys Ser Arg Leu Asn Ser Trp Phe Gln His Arg
        275                 280                 285

Pro Pro Gly Ala Pro Pro Glu Arg Tyr Leu Gly Leu Pro Gly Ser Leu
    290                 295                 300

Lys Trp Glu Asp Arg Gly Pro Ser Gly Gln Gly Gln Gly Gln Phe Leu
305                 310                 315                 320

Ile Gln Gln Val Thr Leu Lys Ile Pro Ile Ser Ile Glu Phe Val Phe
                325                 330                 335

Glu Ser Gly Ser Ala Gln Ala Gly Gly Asn Gln Ala Leu Pro Arg Leu
            340                 345                 350

Ala Gly Ser Leu Leu Thr Gln Ala Leu Glu Ser His Ala Glu Gly Phe
        355                 360                 365

Arg Glu Arg Phe Glu Lys Thr Phe Gln Leu Lys Glu Lys Gly Leu Ser
    370                 375                 380

Ser Gly Glu Gln Val Leu Gly Gln Ala Ala Leu Ser Gly Leu Leu Gly
385                 390                 395                 400

Gly Ile Gly Tyr Phe Tyr Gly Gln Gly Leu Val Leu Pro Asp Ile Gly
                405                 410                 415

Val Glu Gly Ser Glu Gln Lys Val Asp Pro Ala Leu Phe Pro Pro Val
            420                 425                 430

Pro Leu Phe Thr Ala Val Pro Ser Arg Ser Phe Phe Pro Arg Gly Phe
        435                 440                 445

Leu Trp Asp Glu Gly Phe His Gln Leu Val Val Gln Arg Trp Asp Pro
    450                 455                 460

Ser Leu Thr Arg Glu Ala Leu Gly His Trp Leu Gly Leu Leu Asn Ala
465                 470                 475                 480

Asp Gly Trp Ile Gly Arg Glu Gln Ile Leu Gly Asp Glu Ala Arg Ala
                485                 490                 495

Arg Val Pro Pro Glu Phe Leu Val Gln Arg Ala Val His Ala Asn Pro
            500                 505                 510

Pro Thr Leu Leu Leu Pro Val Ala His Met Leu Glu Val Gly Asp Pro
        515                 520                 525

Asp Asp Leu Ala Phe Leu Arg Lys Ala Leu Pro Arg Leu His Ala Trp
    530                 535                 540

Phe Ser Trp Leu His Gln Ser Gln Ala Gly Pro Leu Pro Leu Ser Tyr
545                 550                 555                 560

Arg Trp Arg Gly Arg Asp Pro Ala Leu Pro Thr Leu Leu Asn Pro Lys
                565                 570                 575

Thr Leu Pro Ser Gly Leu Asp Asp Tyr Pro Arg Ala Ser His Pro Ser
            580                 585                 590
```

```
Val Thr Glu Arg His Leu Asp Leu Arg Cys Trp Val Ala Leu Gly Ala
        595                 600                 605

Arg Val Leu Thr Arg Leu Ala Glu His Leu Gly Glu Ala Glu Val Ala
    610                 615                 620

Ala Glu Leu Gly Pro Leu Ala Ala Ser Leu Glu Ala Ala Glu Ser Leu
625                 630                 635                 640

Asp Glu Leu His Trp Ala Pro Glu Leu Gly Val Phe Ala Asp Phe Gly
                645                 650                 655

Asn His Thr Lys Ala Val Gln Leu Lys Pro Arg Pro Pro Gln Gly Leu
            660                 665                 670

Val Arg Val Val Gly Arg Pro Gln Pro Gln Leu Gln Tyr Val Asp Ala
        675                 680                 685

Leu Gly Tyr Val Ser Leu Phe Pro Leu Leu Leu Arg Leu Leu Asp Pro
    690                 695                 700

Thr Ser Ser Arg Leu Gly Pro Leu Leu Asp Ile Leu Ala Asp Ser Arg
705                 710                 715                 720

His Leu Trp Ser Pro Phe Gly Leu Arg Ser Leu Ala Ala Ser Ser Ser
                725                 730                 735

Phe Tyr Gly Gln Arg Asn Ser Glu His Asp Pro Pro Tyr Trp Arg Gly
            740                 745                 750

Ala Val Trp Leu Asn Val Asn Tyr Leu Ala Leu Gly Ala Leu His His
        755                 760                 765

Tyr Gly His Leu Glu Gly Pro His Gln Ala Arg Ala Ala Lys Leu His
    770                 775                 780

Gly Glu Leu Arg Ala Asn Val Val Gly Asn Val Trp Arg Gln Tyr Gln
785                 790                 795                 800

Ala Thr Gly Phe Leu Trp Glu Gln Tyr Ser Asp Arg Asp Gly Arg Gly
                805                 810                 815

Met Gly Cys Arg Pro Phe His Gly Trp Thr Ser Leu Val Leu Leu Ala
            820                 825                 830

Met Ala Glu Asp Tyr His His His His His His
        835                 840
```

<210> SEQ ID NO 2
<211> LENGTH: 976
<212> TYPE: PRT
<213> ORGANISM: Artificial Sequence
<220> FEATURE:
<223> OTHER INFORMATION: Alpha subunit of full-length murine glucosidase II

<400> SEQUENCE: 2

```
Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Ala
            20                  25                  30

Val Asp Arg Ser Asn Phe Lys Thr Cys Asp Glu Ser Ser Phe Cys Lys
        35                  40                  45

Arg Gln Arg Ser Ile Arg Pro Gly Leu Ser Pro Tyr Arg Ala Leu Leu
    50                  55                  60

Asp Thr Leu Gln Leu Gly Pro Asp Ala Leu Thr Val His Leu Ile His
65                  70                  75                  80

Glu Val Thr Lys Val Leu Leu Val Leu Glu Leu Gln Gly Leu Gln Lys
                85                  90                  95

Asn Met Thr Arg Ile Arg Ile Asp Glu Leu Glu Pro Arg Arg Pro Arg
```

-continued

```
            100                 105                 110

Tyr Arg Val Pro Asp Val Leu Val Ala Asp Pro Pro Thr Ala Arg Leu
        115                 120                 125

Ser Val Ser Gly Arg Asp Asp Asn Ser Val Glu Leu Thr Val Ala Glu
    130                 135                 140

Gly Pro Tyr Lys Ile Ile Leu Thr Ala Gln Pro Phe Arg Leu Asp Leu
145                 150                 155                 160

Leu Glu Asp Arg Ser Leu Leu Leu Ser Val Asn Ala Arg Gly Leu Met
                165                 170                 175

Ala Phe Glu His Gln Arg Ala Pro Arg Val Pro Phe Ser Asp Lys Val
            180                 185                 190

Ser Leu Ala Leu Gly Ser Val Trp Asp Lys Ile Lys Asn Leu Phe Ser
        195                 200                 205

Arg Gln Glu Ser Lys Asp Pro Ala Glu Gly Asn Gly Ala Gln Pro Glu
    210                 215                 220

Ala Thr Pro Gly Asp Gly Asp Lys Pro Glu Glu Thr Gln Glu Lys Ala
225                 230                 235                 240

Glu Lys Asp Glu Pro Gly Ala Trp Glu Glu Thr Phe Lys Thr His Ser
                245                 250                 255

Asp Ser Lys Pro Tyr Gly Pro Thr Ser Val Gly Leu Asp Phe Ser Leu
            260                 265                 270

Pro Gly Met Glu His Val Tyr Gly Ile Pro Glu His Ala Asp Ser Leu
        275                 280                 285

Arg Leu Lys Val Thr Glu Gly Gly Glu Pro Tyr Arg Leu Tyr Asn Leu
    290                 295                 300

Asp Val Phe Gln Tyr Glu Leu Asn Asn Pro Met Ala Leu Tyr Gly Ser
305                 310                 315                 320

Val Pro Val Leu Leu Ala His Ser Phe His Arg Asp Leu Gly Ile Phe
                325                 330                 335

Trp Leu Asn Ala Ala Glu Thr Trp Val Asp Ile Ser Ser Asn Thr Ala
            340                 345                 350

Gly Lys Thr Leu Phe Gly Lys Met Leu Asp Tyr Leu Gln Gly Ser Gly
        355                 360                 365

Glu Thr Pro Gln Thr Asp Ile Arg Trp Met Ser Glu Ser Gly Ile Ile
    370                 375                 380

Asp Val Phe Leu Met Leu Gly Pro Ser Val Phe Asp Val Phe Arg Gln
385                 390                 395                 400

Tyr Ala Ser Leu Thr Gly Thr Gln Ala Leu Pro Pro Leu Phe Ser Leu
                405                 410                 415

Gly Tyr His Gln Ser Arg Trp Asn Tyr Arg Asp Glu Ala Asp Val Leu
            420                 425                 430

Glu Val Asp Gln Gly Phe Asp Asp His Asn Met Pro Cys Asp Val Ile
        435                 440                 445

Trp Leu Asp Ile Glu His Ala Asp Gly Lys Arg Tyr Phe Thr Trp Asp
    450                 455                 460

Pro Thr Arg Phe Pro Gln Pro Leu Asn Met Leu Glu His Leu Ala Ser
465                 470                 475                 480

Lys Arg Arg Lys Leu Val Ala Ile Val Asp Pro His Ile Lys Val Asp
                485                 490                 495

Ser Gly Tyr Arg Val His Glu Glu Leu Arg Asn His Gly Leu Tyr Val
            500                 505                 510

Lys Thr Arg Asp Gly Ser Asp Tyr Glu Gly Trp Cys Trp Pro Gly Ser
        515                 520                 525
```

-continued

```
Ala Ser Tyr Pro Asp Phe Thr Asn Pro Arg Met Arg Ala Trp Trp Ser
    530                 535                 540

Asn Met Phe Ser Phe Asp Asn Tyr Glu Gly Ser Ala Pro Asn Leu Tyr
545                 550                 555                 560

Val Trp Asn Asp Met Asn Glu Pro Ser Val Phe Asn Gly Pro Glu Val
                565                 570                 575

Thr Met Leu Lys Asp Ala Val His Tyr Gly Gly Trp Glu His Arg Asp
            580                 585                 590

Ile His Asn Ile Tyr Gly Leu Tyr Val His Met Ala Thr Ala Asp Gly
        595                 600                 605

Leu Ile Gln Arg Ser Gly Gly Ile Glu Arg Pro Phe Val Leu Ser Arg
    610                 615                 620

Ala Phe Phe Ser Gly Ser Gln Arg Phe Gly Ala Val Trp Thr Gly Asp
625                 630                 635                 640

Asn Thr Ala Glu Trp Asp His Leu Lys Ile Ser Ile Pro Met Cys Leu
                645                 650                 655

Ser Leu Ala Leu Val Gly Leu Ser Phe Cys Gly Ala Asp Val Gly Gly
            660                 665                 670

Phe Phe Lys Asn Pro Glu Pro Glu Leu Leu Val Arg Trp Tyr Gln Met
        675                 680                 685

Gly Ala Tyr Gln Pro Phe Phe Arg Ala His Ala His Leu Asp Thr Gly
    690                 695                 700

Arg Arg Glu Pro Trp Leu Leu Ala Ser Gln Tyr Gln Asp Ala Ile Arg
705                 710                 715                 720

Asp Ala Leu Phe Gln Arg Tyr Ser Leu Leu Pro Phe Trp Tyr Thr Leu
                725                 730                 735

Phe Tyr Gln Ala His Lys Glu Gly Phe Pro Val Met Arg Pro Leu Trp
            740                 745                 750

Val Gln Tyr Pro Glu Asp Met Ser Thr Phe Ser Ile Glu Asp Gln Phe
        755                 760                 765

Met Leu Gly Asp Ala Leu Leu Ile His Pro Val Ser Asp Ala Gly Ala
    770                 775                 780

His Gly Val Gln Val Tyr Leu Pro Gly Gln Glu Glu Val Trp Tyr Asp
785                 790                 795                 800

Ile Gln Ser Tyr Gln Lys His His Gly Pro Gln Thr Leu Tyr Leu Pro
                805                 810                 815

Val Thr Leu Ser Ser Ile Pro Val Phe Gln Arg Gly Gly Thr Ile Val
            820                 825                 830

Pro Arg Trp Met Arg Val Arg Arg Ser Ser Asp Cys Met Lys Asp Asp
        835                 840                 845

Pro Ile Thr Leu Phe Val Ala Leu Ser Pro Gln Gly Thr Ala Gln Gly
    850                 855                 860

Glu Leu Phe Leu Asp Asp Gly His Thr Phe Asn Tyr Gln Thr Arg His
865                 870                 875                 880

Glu Phe Leu Leu Arg Arg Phe Ser Phe Ser Gly Ser Thr Leu Val Ser
                885                 890                 895

Ser Ser Ala Asp Pro Lys Gly His Leu Glu Thr Pro Ile Trp Ile Glu
            900                 905                 910

Arg Val Val Ile Met Gly Ala Gly Lys Pro Ala Ala Val Val Leu Gln
        915                 920                 925

Thr Lys Gly Ser Pro Glu Ser Arg Leu Ser Phe Gln His Asp Pro Glu
    930                 935                 940
```

-continued

Thr Ser Val Leu Ile Leu Arg Lys Pro Gly Val Ser Val Ala Ser Asp
945 950 955 960

Trp Ser Ile His Leu Arg Ala Ser Trp Ser His Pro Gln Phe Glu Lys
965 970 975

<210> SEQ ID NO 3
<211> LENGTH: 542
<212> TYPE: PRT
<213> ORGANISM: Artificial Sequence
<220> FEATURE:
<223> OTHER INFORMATION: Beta subunit of full-length murine glucosidase II

<400> SEQUENCE: 3

Met Gly Ile Leu Pro Ser Pro Gly Met Pro Ala Leu Leu Ser Leu Val
1 5 10 15

Ser Leu Leu Ser Val Leu Leu Met Gly Cys Val Ala Glu Thr Gly Ala
20 25 30

Val Glu Val Lys Arg Pro Arg Gly Val Ser Leu Ser Asn His His Phe
35 40 45

Tyr Glu Glu Ser Lys Pro Phe Thr Cys Leu Asp Gly Thr Ala Thr Ile
50 55 60

Pro Phe Asp Gln Val Asn Asp Asp Tyr Cys Asp Cys Lys Asp Gly Ser
65 70 75 80

Asp Glu Pro Gly Thr Ala Ala Cys Pro Asn Gly Ser Phe His Cys Thr
85 90 95

Asn Thr Gly Tyr Lys Pro Leu Tyr Ile Leu Ser Ser Arg Val Asn Asp
100 105 110

Gly Val Cys Asp Cys Cys Asp Gly Thr Asp Glu Tyr Asn Ser Gly Thr
115 120 125

Val Cys Glu Asn Thr Cys Arg Glu Lys Gly Arg Lys Glu Lys Glu Ser
130 135 140

Leu Gln Gln Leu Ala Glu Val Thr Arg Glu Gly Phe Arg Leu Lys Lys
145 150 155 160

Ile Leu Ile Glu Glu Trp Lys Thr Ala Arg Glu Glu Lys Gln Ser Lys
165 170 175

Leu Leu Glu Leu Gln Ala Gly Lys Lys Ser Leu Glu Asp Gln Val Glu
180 185 190

Thr Leu Arg Ala Ala Lys Glu Glu Ala Glu Arg Pro Glu Lys Glu Ala
195 200 205

Lys Asp Gln His Arg Lys Leu Trp Glu Glu Gln Gln Ala Ala Ala Lys
210 215 220

Ala Arg Arg Glu Gln Glu Arg Ala Ala Ser Ala Phe Gln Glu Leu Asp
225 230 235 240

Asp Asn Met Asp Gly Met Val Ser Leu Ala Glu Leu Gln Thr His Pro
245 250 255

Glu Leu Asp Thr Asp Gly Asp Gly Ala Leu Ser Glu Glu Glu Ala Gln
260 265 270

Ala Leu Leu Ser Gly Asp Thr Gln Thr Asp Thr Thr Ser Phe Tyr Asp
275 280 285

Arg Val Trp Ala Ala Ile Arg Asp Lys Tyr Arg Ser Glu Val Pro Pro
290 295 300

Thr Asp Ile Pro Val Pro Glu Glu Thr Glu Pro Lys Glu Glu Lys Pro
305 310 315 320

Pro Val Leu Pro Pro Thr Glu Glu Glu Glu Glu Glu Glu Glu Glu Pro
325 330 335

-continued

```
Glu Glu Glu Glu Glu Glu Glu Glu Glu Glu Glu Glu Ala Pro Pro Pro
            340                 345                 350

Leu Gln Pro Pro Gln Pro Pro Ser Pro Thr Glu Asp Glu Lys Met Pro
        355                 360                 365

Pro Tyr Asp Glu Glu Thr Gln Ala Ile Ile Asp Ala Ala Gln Glu Ala
    370                 375                 380

Arg Ser Lys Phe Glu Glu Val Glu Arg Ser Leu Lys Glu Met Glu Glu
385                 390                 395                 400

Ser Ile Arg Ser Leu Glu Gln Glu Ile Ser Phe Asp Phe Gly Pro Ser
                405                 410                 415

Gly Glu Phe Ala Tyr Leu Tyr Ser Gln Cys Tyr Glu Leu Thr Thr Asn
            420                 425                 430

Glu Tyr Val Tyr Arg Leu Cys Pro Phe Lys Leu Val Ser Gln Lys Pro
        435                 440                 445

Lys His Gly Gly Ser Pro Thr Ser Leu Gly Thr Trp Gly Ser Trp Ala
    450                 455                 460

Gly Pro Asp His Asp Lys Phe Ser Ala Met Lys Tyr Glu Gln Gly Thr
465                 470                 475                 480

Gly Cys Trp Gln Gly Pro Asn Arg Ser Thr Thr Val Arg Leu Leu Cys
                485                 490                 495

Gly Lys Glu Thr Val Val Thr Ser Thr Thr Glu Pro Ser Arg Cys Glu
            500                 505                 510

Tyr Leu Met Glu Leu Met Thr Pro Ala Ala Cys Pro Glu Pro Pro Pro
        515                 520                 525

Glu Ala Pro Ser Asp Gly Asp Lys His His His His His His
    530                 535                 540
```